United States Patent
Mishra

(10) Patent No.: US 10,214,727 B2
(45) Date of Patent: Feb. 26, 2019

(54) PLATELET-RICH PLASMA COMPOSITIONS AND METHODS OF PREPARATION

(71) Applicant: Allan Mishra, Menlo Park, CA (US)

(72) Inventor: Allan Mishra, Menlo Park, CA (US)

( * ) Notice: Subject to any disclaimer, the term of this patent is extended or adjusted under 35 U.S.C. 154(b) by 145 days.

(21) Appl. No.: 15/413,931

(22) Filed: Jan. 24, 2017

(65) Prior Publication Data
US 2017/0130201 A1    May 11, 2017

Related U.S. Application Data

(63) Continuation of application No. 14/292,658, filed on May 30, 2014.

(60) Provisional application No. 61/830,754, filed on Jun. 4, 2013.

(51) Int. Cl.
| | | |
|---|---|---|
| *C12N 15/00* | (2006.01) | |
| *C12N 5/078* | (2010.01) | |
| *C12N 5/074* | (2010.01) | |
| *C12N 5/079* | (2010.01) | |

(52) U.S. Cl.
CPC ......... *C12N 5/0644* (2013.01); *C12N 5/0622* (2013.01); *C12N 5/0696* (2013.01); *C12N 2502/11* (2013.01); *C12N 2502/115* (2013.01); *C12N 2506/1307* (2013.01)

(58) Field of Classification Search
CPC .. C12N 5/0644; C12N 5/0622; C12N 5/0696; C12N 2502/11; C12N 2506/1307
USPC .......................................................... 435/455
See application file for complete search history.

(56) References Cited

U.S. PATENT DOCUMENTS

| | | | |
|---|---|---|---|
| 4,081,331 | A | 3/1978 | Weiss |
| 4,414,108 | A | 11/1983 | Ito et al. |
| 4,663,289 | A | 5/1987 | Veech |
| 4,931,395 | A | 6/1990 | Griffin |
| 4,936,998 | A | 6/1990 | Nishimura et al. |
| 4,957,742 | A | 9/1990 | Knighton |
| 5,079,236 | A | 1/1992 | Drizen et al. |
| 5,124,316 | A | 6/1992 | Antoniades et al. |
| 5,147,776 | A | 9/1992 | Koerner, Jr. |
| 5,165,938 | A | 11/1992 | Knighton |
| 5,178,883 | A | 1/1993 | Knighton |
| 5,209,724 | A | 5/1993 | Dhaliwal et al. |
| 5,269,290 | A | 12/1993 | Barrett et al. |
| 5,313,953 | A | 5/1994 | Yomtov et al. |
| 5,336,387 | A | 8/1994 | Egen et al. |
| 5,385,937 | A | 1/1995 | Stamler et al. |
| 5,403,272 | A | 4/1995 | Deniega et al. |
| 5,449,688 | A | 9/1995 | Wahl et al. |
| 5,474,891 | A | 12/1995 | Murphy |
| 5,494,590 | A | 2/1996 | Smith et al. |
| 5,501,795 | A | 3/1996 | Pall et al. |
| 5,510,102 | A | 4/1996 | Cochrum |
| 5,578,460 | A | 11/1996 | Ebersole et al. |
| 5,578,565 | A | 11/1996 | Chao et al. |
| 5,585,007 | A | 12/1996 | Antanavich et al. |
| 5,599,558 | A | 2/1997 | Gordinier et al. |
| 5,607,691 | A | 3/1997 | Hale et al. |
| 5,614,204 | A | 3/1997 | Cochrum |
| 5,614,214 | A | 3/1997 | Ahl et al. |
| 5,618,663 | A | 4/1997 | Delmas |
| 5,643,786 | A | 7/1997 | Cohen et al. |
| 5,676,849 | A | 10/1997 | Sammons et al. |
| 5,733,545 | A | 3/1998 | Hood |
| 5,773,033 | A | 6/1998 | Cochrum et al. |
| 5,785,869 | A | 7/1998 | Martinson et al. |
| 5,788,662 | A | 8/1998 | Antanavich et al. |
| 5,834,418 | A | 11/1998 | Brazeau et al. |
| 5,905,142 | A | 5/1999 | Murray |
| 5,906,570 | A | 5/1999 | Langley et al. |
| 5,916,743 | A | 6/1999 | Lake et al. |
| 5,928,214 | A | 7/1999 | Rubinstein et al. |
| 5,935,850 | A | 8/1999 | Clark et al. |
| 5,993,804 | A | 11/1999 | Read et al. |
| 6,063,297 | A | 5/2000 | Antanavich et al. |
| 6,098,631 | A | 8/2000 | Holoshitz et al. |
| 6,102,926 | A | 8/2000 | Tartaglia et al. |
| 6,120,520 | A | 9/2000 | Saadat et al. |
| 6,132,396 | A | 10/2000 | Antanavich et al. |
| 6,183,442 | B1 | 2/2001 | Athanasiou et al. |
| 6,210,976 | B1 | 4/2001 | Sabbadini |
| 6,214,338 | B1 | 4/2001 | Antanavich et al. |
| 6,242,594 | B1 | 6/2001 | Kelly |

(Continued)

FOREIGN PATENT DOCUMENTS

| | | |
|---|---|---|
| DE | 19747149 A1 | 5/1999 |
| EP | 0142339 | 5/1985 |

(Continued)

OTHER PUBLICATIONS

"Formulating." Dictionary.com Unabridged (v 1.1). Random House, Inc. Apr. 16, 2009. (Dictionary.com http://dictionary.reference.com/browse/formulating).

Arnar et al., Am J Physiol. Heart Circ. Physiol., 2002, vol. 282, p. H1189-H1196.

Asanuma, et al., The Hydrogen Ion Concentration (pH) in Blood Samples With K2EDTA and K3EDTA Affects Mean Corpuscular Volume Values in Hemodialysis Patients, Laboratory Hematology, 2000, vol. 6, pp. 67-72.

Aster et al., "The Anticoagulants of Choice for Platelet Transfusions", Transfusion 6 (1) : 32-38 (1966).

Atherton, "Acid-base balance: maintenance of plasma pH", Anaesthesia and Intensive Care Medicine, pp. 419-422 (2003).

Badgett et al., "Interferon-gamma modulates lung macrophage production of PDGF-BB and fibroblast growth", J. Lipid Mediators and Cell Signalling 13 (1): 89-97 (1996), Biosis abstract only.

(Continued)

*Primary Examiner* — Valarie Bertoglio
(74) *Attorney, Agent, or Firm* — Knobbe, Martens, Olson & Bear LLP

(57) ABSTRACT

Methods of preparing platelet-rich plasma (PRP) compositions are disclosed which include adding CD34+ cells to the PRP composition. In addition, the concentration of stromal-derived factor-1 (SDF-1) in the PRP composition may be adjusted to a pre-determined value. The compositions may have elevated levels of white blood cells but reduced levels of neutrophils. Compositions produced by the method are also disclosed.

11 Claims, 1 Drawing Sheet

(56) References Cited

U.S. PATENT DOCUMENTS

| | | |
|---|---|---|
| 6,280,473 B1 | 8/2001 | Lemperle et al. |
| 6,306,171 B1 | 10/2001 | Conzemius |
| 6,315,992 B1 | 11/2001 | Noh et al. |
| 6,322,785 B1 | 11/2001 | Landesberg et al. |
| 6,425,887 B1 | 7/2002 | McGuckin et al. |
| 6,432,119 B1 | 8/2002 | Saadat |
| 6,444,228 B1 | 9/2002 | Baugh et al. |
| 6,447,443 B1 | 9/2002 | Keogh et al. |
| 6,454,804 B1 | 9/2002 | Ferree |
| 6,596,179 B2 | 7/2003 | Giesler et al. |
| 6,712,851 B1 | 3/2004 | Lemperle et al. |
| 6,811,777 B2 | 11/2004 | Mishra |
| 6,837,848 B2 | 1/2005 | Bonner et al. |
| 6,905,612 B2 | 6/2005 | Dorian et al. |
| 6,942,639 B2 | 9/2005 | Baugh et al. |
| 6,942,880 B1 | 9/2005 | Dolecek et al. |
| 7,169,547 B2 | 1/2007 | Rubinstein et al. |
| 7,179,249 B2 | 2/2007 | Steward et al. |
| 7,211,191 B2 | 5/2007 | Coelho et al. |
| 7,252,758 B2 | 8/2007 | Dolecek et al. |
| 7,314,617 B2 | 1/2008 | Mishra |
| 7,462,268 B2 | 12/2008 | Mishra |
| 7,608,258 B2 | 10/2009 | Mishra |
| 7,708,152 B2 | 5/2010 | Dorian et al. |
| 8,142,993 B1 | 3/2012 | Mishra |
| 8,163,277 B2 | 4/2012 | Mishra |
| 8,440,459 B2 | 5/2013 | Mishra |
| 8,444,969 B2 | 5/2013 | Mishra |
| 2001/0031978 A1 | 10/2001 | Kipke et al. |
| 2002/0004038 A1 | 1/2002 | Baugh et al. |
| 2002/0006437 A1 | 1/2002 | Grooms et al. |
| 2002/0032155 A1 | 3/2002 | Ferree |
| 2002/0058030 A1 | 5/2002 | Monroy et al. |
| 2002/0082220 A1 | 6/2002 | Hoemann et al. |
| 2002/0147611 A1 | 10/2002 | Greene et al. |
| 2003/0007957 A1 | 1/2003 | Britton et al. |
| 2003/0116512 A1 | 6/2003 | Antwiller et al. |
| 2003/0143211 A1 | 7/2003 | Intini et al. |
| 2003/0152639 A1 | 8/2003 | Britton et al. |
| 2003/0175248 A1 | 9/2003 | Uhr |
| 2003/0185812 A1 | 10/2003 | Ferree |
| 2003/0191005 A1 | 10/2003 | Coelho et al. |
| 2003/0192554 A1 | 10/2003 | Ferree |
| 2003/0205538 A1 | 11/2003 | Dorian et al. |
| 2003/0224455 A1 | 12/2003 | Abbracchio et al. |
| 2003/0233064 A1 | 12/2003 | Arm et al. |
| 2003/0236573 A1 | 12/2003 | Evans et al. |
| 2004/0022864 A1 | 2/2004 | Freyman et al. |
| 2004/0073223 A1 | 4/2004 | Burkinshaw |
| 2004/0091459 A1 | 5/2004 | Nimni |
| 2004/0126885 A1 | 7/2004 | Cines et al. |
| 2004/0131583 A1 | 7/2004 | Barritault et al. |
| 2004/0182795 A1 | 9/2004 | Dorian et al. |
| 2004/0220101 A1 | 11/2004 | Ferree |
| 2004/0220102 A1 | 11/2004 | Ferree |
| 2004/0244806 A1 | 12/2004 | Ferree |
| 2005/0043738 A1 | 2/2005 | Ryan |
| 2005/0064042 A1 | 3/2005 | Vunjak-Novakovic et al. |
| 2005/0107323 A1 | 5/2005 | Donahue et al. |
| 2005/0186193 A1 | 8/2005 | Mishra |
| 2005/0209081 A1 | 9/2005 | Baugh et al. |
| 2005/0209564 A1 | 9/2005 | Bonner et al. |
| 2006/0029578 A1 | 2/2006 | Hoemann et al. |
| 2006/0041243 A1 | 2/2006 | Nayak et al. |
| 2006/0064101 A1 | 3/2006 | Arramon |
| 2006/0068369 A1 | 3/2006 | Coelho et al. |
| 2006/0127382 A1 | 6/2006 | Mishra |
| 2006/0134599 A1 | 6/2006 | Toner et al. |
| 2006/0200081 A1 | 9/2006 | Mizus |
| 2006/0235306 A1 | 10/2006 | Cotter et al. |
| 2007/0014784 A1 | 1/2007 | Nayak et al. |
| 2007/0020735 A1 | 1/2007 | Chen et al. |
| 2007/0037737 A1 | 2/2007 | Hoemann et al. |
| 2007/0042016 A1 | 2/2007 | Nayak et al. |
| 2007/0087061 A1 | 4/2007 | Drake et al. |
| 2007/0110737 A1 | 5/2007 | Mishra |
| 2007/0122906 A1 | 5/2007 | Mishra |
| 2007/0172472 A1 | 7/2007 | Nayak |
| 2007/0178073 A1 | 8/2007 | Chang et al. |
| 2007/0179424 A1 | 8/2007 | Rubinstein et al. |
| 2007/0202093 A1 | 8/2007 | Brooks et al. |
| 2007/0269887 A1 | 11/2007 | Coelho et al. |
| 2008/0045964 A1 | 2/2008 | Mishra |
| 2008/0069777 A1 | 3/2008 | Cohen et al. |
| 2008/0081367 A1 | 4/2008 | Sowemimo-Coker et al. |
| 2008/0089867 A1 | 4/2008 | Fernandes et al. |
| 2008/0248081 A1 | 10/2008 | Mishra |
| 2008/0248082 A1 | 10/2008 | Mishra |
| 2008/0248083 A1 | 10/2008 | Mishra |
| 2008/0248084 A1 | 10/2008 | Mishra |
| 2008/0248085 A1 | 10/2008 | Mishra |
| 2008/0255471 A1 | 10/2008 | Naghavi et al. |
| 2009/0005733 A1 | 1/2009 | Chiu et al. |
| 2009/0053208 A1 | 2/2009 | Nayak |
| 2009/0092679 A1 | 4/2009 | Mishra |
| 2009/0227952 A1 | 9/2009 | Blakstvedt et al. |
| 2009/0254104 A1 | 10/2009 | Murray |
| 2010/0112081 A1 | 5/2010 | Mishra et al. |
| 2010/0120144 A1 | 5/2010 | Mishra |
| 2010/0140182 A1 | 6/2010 | Chapman et al. |
| 2010/0150892 A1 | 6/2010 | Han |
| 2010/0183561 A1 | 7/2010 | Sakthivel et al. |
| 2010/0196497 A1 | 8/2010 | Lim et al. |
| 2010/0233282 A1 | 9/2010 | Mishra |
| 2013/0017180 A1 | 1/2013 | Mishra |
| 2013/0177623 A1 | 7/2013 | Bowlin et al. |
| 2013/0197468 A1 | 8/2013 | Schwartzman et al. |
| 2013/0243879 A1 | 9/2013 | Mishra |
| 2014/0295555 A1 | 10/2014 | Mishra |
| 2014/0356893 A1 | 12/2014 | Mishra |
| 2016/0106779 A1 | 4/2016 | Mishra |
| 2016/0367599 A1 | 12/2016 | Mishra |
| 2017/0020923 A1 | 1/2017 | Mishra |

FOREIGN PATENT DOCUMENTS

| | | |
|---|---|---|
| EP | 0417818 | 3/1991 |
| EP | 2258379 | 12/2010 |
| JP | 61-502943 | 12/1986 |
| JP | 5-500516 | 2/1993 |
| WO | WO 91/04035 | 4/1991 |
| WO | WO 00/01427 | 1/2000 |
| WO | WO 00/12018 | 3/2000 |
| WO | WO 00/54661 | 9/2000 |
| WO | WO 01/43756 A2 | 6/2001 |
| WO | WO 02/13683 | 2/2002 |
| WO | WO 02/015904 | 2/2002 |
| WO | WO 03/015800 | 2/2003 |
| WO | WO 03/090839 A1 | 11/2003 |
| WO | WO 2004/012795 A2 | 2/2004 |
| WO | WO 2004/022078 | 3/2004 |
| WO | WO 2005/044154 | 5/2005 |
| WO | WO 2005/065242 | 7/2005 |
| WO | WO 2007/112135 | 10/2007 |
| WO | WO 2011/127071 | 10/2011 |

OTHER PUBLICATIONS

Balk, et al. "Outcome of Surgery for Lateral Epicondylitis (Tennis Elbow): Effect of Worker's Compensation," The American Journal of Orthopedics, pp. 122-126, Mar. 2005.

Barrett, et al. "Growth Factors for Chronic Plantar Fasciitis?" Podiatry Today, pp. 37-42, Nov. 2004.

Berg et al., "Platelets induce reactive oxygen species-dependent growth of human skin fibroblasts" European J. Cell Biology 82 : 565-571 (2003).

Boldt et al. "Acute platelet-rich plasmapheresis for cardiac surgery" Journal of Cardiothoracic and Vascular Anesthesia, Saunders, Philadelphia, PA, U.S., vol. 9, No. 1, Feb. 1, 1995 (Feb. 1, 1995), pp. 79-88, XP005227129, ISSN: 1053-0770, LNKD-DOI:10.1016/S1053-0770(05)80061-8.

(56) References Cited

OTHER PUBLICATIONS

CD15 MicroBeads, Miltenyi Biotec Inc., downloaded from www.miltenyibiotec.com, pp. 4.
Cell Factor Technologies, Inc., Brochure for Boost Demineralizedbonematrix, 6 pages, 2004.
Cell Factor Technologies, Inc., Brochure for GPS II Platelet Concentrate System, 10 pages, 2004.
Chen, et al., PMA-activated Neutrophils Decrease Pulmonary Endothelial Ectoenzyme Activities in Perfused Rabbit Lungs, American Journal of Physiology, Dec. 1992, vol. 263, Issue 6, pp. L650-L656.
Cohen, et al. "Wound Care and Wound Healing," in Principles of Surgery, Chapter 8 (Seymore, et al. eds.) pp. 263-295, New York, 1999.
Colditz, et al., Neutrophil Accumulation and Plasma Leakage Induced in vivo by Neutrophil-Activating Peptide-1, Journal of Leukocyte Biology, 1990, vol. 48, pp. 129-137.
Coller, et al. "The pH Dependence of Quantitative Ristocetin-Induced Platelet Aggregation: Theoretical and Practical Implications—a New Device for Maintenance of Platelet-Rich Plasma pH," Blood, vol. 47, No. 5, pp. 841-854, May 1976.
Cook, et al. "Overuse Tendinosis, Not Tendinitis, Part 2: Applying the New Approach to Patellar Tendinopathy," The Physician and Sportsmedicine, vol. 28, No. 6, 12 pages, Jun. 2000.
Cotter et al., "A Novel Method for Isolation of Neutrophils from Murine Blood Using Negative Immunomagnetic Separation," The American Journal of Pathology, vol. 159, pp. 473-481, 2001.
Cupo et al., "Acute left ventricular dysfunction of severe scorpion envenomation is related to myocardial perfusion disturbance," International J. Cardiology., vol. 116(1), pp. 98-106 (2007), abstract only.
Davies, Tennis Elbow, http://www.3-rx.com/tenniselbow/treatment.php, May 4, 2001, accessed Dec. 11, 2008.
DePuy AcroMed, Inc. Brochure for Symphony Platelet Concentrate System, 10 pages, 2001.
Djuric and Ellis (Stem Cell Research and Therapy, 2010, 1 :3, pp. 1-6).
Douketis et al., The Perioperative Management of Antithrombotic Therapy, Chest 133(6):299-339S, Jun. 2008, Supplement.
Durukan, et al. "Acute Ischemic Stroke: Overview of Major Experimental Rodent Models, Pathophysiology, and Therapy of Focal Cerebral Ischemia," Pharmacology, Biochemistry and Behavoir, 87:179-197, 2007.
Edwards et al., "Autologous Blood Injections for Refractory Lateral Epicondylitis," The Journal of Hand Surgery, vol. 28A, No. 2, pp. 272-278, Mar. 2003.
Ehrenfest, et al. "Classification of Platelet Concentrates: from Pure Platelet-rich Plasma (P-PRP) to Leucocyte- and Platelet-rich Fibrin (L-PRF)," Trends in Biotechnology, vol. 27, No. 3, pp. 158-167, 2008.
Eppley et al. "Platelet Quantification and Growth Factor Analysis from Platelet-Rich Plasma: Implications for Wound Healing," Plastic and Reconstructive Surgery, pp. 1502-1508, vol. 114, No. 6, Nov. 2004.
Esa et al., "Immunological Heterogeneity of Human Monocyte Subsets Prepared by Counterflow Centrifugation Elutriation," Immunology, vol. 59, pp. 95-99, 1986.
European Office Third Party Observations for EP 1494535 dated Apr. 9, 2015.
European Patent Examination dated Jul. 6, 2015 for EP 09819913.6.
Extended European Search Report issued in European Patent Application No. 09819913.6, dated May 10, 2013.
Farrugia et al., "Red cell and platelet concentrates from blood collected into half-strength citrate anticoagulant: improved maintenance of red cell 2,3-diphosphoglycerate in half-citrate red cells" Vox Sanguinis 63 (1) : 31-38 (1992), abstract only.
Feng et al., "Treatment of Osseous Defects With Fibroblast-Coated Hydroxylapatite Particles" J. Formosan Med. Assoc. 91 1068-1074 (1992).

Feuerstein et al. "Congestive Heart Failure and Genomic Medicine: A Look into the 21st Century," Cardiovascular Drugs and Therapy, vol. 11, No. 6, pp. 713-717, 1997.
Fijnheer et al., "Platelet activation during preparation of platelet concentrates: a comparison of the platelet-rich plasma and the buffy coat methods," Transfusion, vol. 30(7), pp. 634-638 (1990).
Floryan et al., "Home Study Program: Intraoperative Use of Autologous Platelet-Rich and Platelet-Poor Plasma for Orthopedic Surgery Patients," Aorn Journal, vol. 80, No. 4, pp. 667-678, Oct. 2004.
Fylling, et al. "Multi-Center Clinical Review: Using Autologous Platelet Gel for the Treatment of Diabetic Plantar Wounds," Diabetes, 50 (Supplement 2), A227 (Jun. 2001).
Gallo et al., "Effect of autologous platelet-rich plasma on heart infarction in sheep," Arch Cardiol Mex., vol. 83(3), pp. 154-158 (Jul.-Sep. 2013).
Gargoyle, 2003, "Chapter 12. Blood", pp. 1-5; Published on the Web—on May 15, 2003 (at http://gargoyle.arcadia.edu/biology/bi327/chapt12.P D F).
Gaudric A. et al., "Use of Autologous Platelet Concentrate in Macular Hole Surgery: Report of 77 Cases"; Macular and Retinal Diseases; Dev Ophthalmology, Basel, Karger; 1997; vol. 29; pp. 30-35.
Gawaz et al. "Platelet Function in Acute Myocardial Infarction Treated with Direct Angioplasty," Circulation, vol. 93, pp. 229-237, 1996 with "Methods, Specimen Collection, Methods, Platelet Aggregation in Vitro, Discussion, Platelet Adhesion to Endothelium in AMI," downloaded from http://circ.ahajournals.org/cgi/content/full/93/2/229 on Dec. 2, 2009.
Gehring et al., "Preparation of autologous platelets for the opthalmologic treatment of macular holes", Transfusion 39: 144-148 (1999).
Gibson et al., "Citrate-Phosphate-Dextrose Solution for Preservation of Human Blood", Transfusion 1 (5) : 280-287 (1961).
Giordano, et al., "Autologous platelet-rich plasma in cardiac surgery: Effect on intraoperative and postoperative transfusion requirements" Journal of Cardiothoracic Anesthesia , XP026263096, ISSN: 0888-6296, LNKD-DOI:10.1016/0888-6296(89)90129-4., Journal of Cardiothoracic Anesthesia, Jun. 1, 1989, vol. 3, Issue 3, pp. 367.
Goel, M.S. and Diamond, S.L. "Neutrophil Enhancement of Fibrin Deposition Under Flow Through Platelet-Dependent and -Independent Mechanisms". Arterioscler Thromb Vasc Biol. 21: 2093-2098, Dec. 2001.
Gruber et al., "Platelets Stimulate Proliferation of Bone Cells: Involvement of Platelet-Derived Growth Factor, Microparticles and Membranes", Clin. Oral Impl. Res, vol. 13, pp. 529-535, 2002.
Guidance for Industry: Biological Product Deviation, Reporting for Blood and Plasma Establishments [online]. Food and Drug Administration, Oct. 2006 [retrieved on Aug. 1, 2013]. Retrieved from the Internet: (URL:http://www.fda.gov/downloads/BiologicsBloodVaccines/GuidanceComplianceRegulatoryInformation/Guidances/Blood/UCM062918.pdf).
Gullung et al., "Platelet-Rich Plasma Effects on Degenerative Disc Disease: Analysis of Histology and Imaging in an Animal Model," 9th Annual AOSpine North America Fellows Forum, Abstract Submission (2011).
Gullung et al., "Platelet-rich plasma effects on degenerative disc disease: analysis of histology and imaging in an animal model," Evidence-Based Spine-Care Journal Web Appendix, vol. 2(4), pp. 1-2 (Nov. 2011).
Gullung et al., "Platelet-rich plasma effects on degenerative disc disease: analysis of histology and imaging in an animal model," Evidence-Based Spine-Care Journal, vol. 2(4), pp. 13-18 (2011).
Harvest Technologies GmbH Brochure for SmartPReP 2, 2002.
Hinkel, "The Effect of Irradiation Upon the Composition and Vascularity of Growing Bones," A.J. Roentgenol and Radium Therap. 50 (4): 516-526 (1943). (Abstract only.).
Hirschi, Annual review of biomedical engineering, 2014, 16:277-294.
http://www.medicinenet.com/connective_tissue disease/article. htm, accessed Jun. 13, 2012. Connective Tissue Disease, pp. 1-3.
http://www.siumed.edu/-dking2/intro/ct.htm#ordinspecial, accessed Jun. 13, 2012. Histological definition of connective tissue from SIU School of Medicine, pp. 1-18.

(56) References Cited

OTHER PUBLICATIONS

Hunzelmann et al., "What are the new milestones in the pathogenesis of systemic sclerosis?", Annals of the Rheumatic Diseases 69 (Suppl 1) i52-i56 (2010), abstract only.
Iba et al. "Angiogenesis by implantation of peripheral blood mononuclear cells and platelets into ischemic limbs", Circulation, 2002, vol. 106, pp. 2019-2025.
International Search Report and Written Opinion in PCT/US09/60061, dated Dec. 9, 2009.
International Search Report and Written Opinion in PCT/US2004/044078, dated Jul. 20, 2005.
Janssen et al., "Experimental animal models in scoliosis research: a review of the literature," The Spine Journal, vol. 11, pp. 347-358 (2011).
Khan et al. "Overuse Tendinosis, Not Tendinitis, Part 1: A New Paradigm for a Difficult Clinical Problem," The Physician and Sportsmedicine, vol. 28, No. 5, 8 pages, May 2000.
Khan, et al. "Histopathology of Common Tendinopathies: Update and Implications for Clinical Management," Clinical Sports Medicine, vol. 27, No. 6, 21 pages (no page numbers) 1999 (downloaded from http://www.clinicalsportsmedicine.com/articles/common_tendinopathies.htm).
Knebel et al., "Heart Failure: State of the Art Treatment and Options," Clinical Nephrology, vol. 60, Suppl. 1, pp. S59-S66 (2003).
Koerner F. et al., "Advances in the Management of Vitreomacular Traction Syndrome and Macular Hole"; Macular and Retinal Diseases; Dev Ophthalmology, Basel, Karger; 1997; vol. 29; pp. 15-29.
Kotov et al., "Regeneration of Human Annulus Fibrosus with Platelet Rich Plasma," Poster Presentation at the American Academy of Orthopedic Surgery meeting in New Orleans (Mar. 2014).
Kurita et al., "Enhanced Vascularization by Controlled Release of Platelet-Rich Plasma Impregnated in Biodegradable Gelatin Hydrogel", Annals of Thoracic Surgery 92 : 837-844 (2011).
Laplante et al., "Mechanisms of wound reepithelialization: hints from a tissue-engineered reconstructed skin to long-standing questions," The FASEB Journal, vol. 15, pp. 2377-2389 (Nov. 2001).
Lee et al., "Cardiac Arrhythmia 2-Catheter ablation of atrial arrhythmias: state of the art," Lancet, vol. 380, pp. 1509-1519 (Oct. 27, 2012).
Levine et al., "Cardiotoxicity and serotonin syndrome complicating a milnacipran overdose," J. Medical Toxicology, vol. 7(4), pp. 312-316 (2011), abstract only.
Li et al., "Effects on Intramyocardial Injection of Platelet-rich Plasma on the Healing Process after Myocardial Infarction," Coronary Artery Disease, vol. 19, Issue 5, pp. 363-370, Aug. 2008.
Lin et al., "Photochemical inactivation of cell-associated human immunodeficiency virus in platelet concentrates", Blood 82: 292-297 (1993).
Liu et al., "Fibroblast proliferation due to exposure to a platelet concentrate in vitro is pH dependent", Wound Repair and Regeneration 10 (5) : 336-340 (2002).
Loder P.B. et al., The Effect of Collagen on Platelet Glycolysis and Nucleotide Metabolism, British Journal of Haematology, 1968, vol. 14, pp. 563-573.
Martinez-Gonzalez et al. "Do Ambulatory-Use Platelet-Rich Plasma (PRP) Concentrates Present Risks," Medicina Oral, vol. 7, pp. 375-390, 2002.
Marx, et al. "Platelet-Rich Plasma, Growth Factor Enhancement for Bone Grafts," Oral Surgery Oral Medicine Oral Pathology, vol. 85, No. 6, pp. 638-646, Jun. 1998.
McCarthy, "New Surgical Options for the Failing Heart," J. of Heart Valve Disease, vol. 8(5), pp. 472-475 (1999).
Metcalfe et al., "Activation during preparation of therapeutic platelets affects deterioration during storage: a comparative flow cytometric study of different production methods," British J. Haematology, vol. 98, pp. 86-95 (1997).
Minamino et al., Endogenous Adenosine Inhibits P-Selectin-dependent Formation of Coronary Thromboemboli during Hypoperfusion in Dogs, Apr. 1998, J. Clin. Invest., vol. 101, No. 8, 1643-1653.
Moki et al., "Effect of platelet-derived growth factors on the proliferation of cultured human tumor cells", Igaku no Ayumi 21 (1) 29-30 (1982), with English translation.
Mooar, et al. "The Efficacy of Autologous Platelet Gel Administration in Total Knee Arthroplasty: An Analysis of Range of Motion, Hemoglobin and Narcotic Requirement," Poster #148 presented at American Academy of Orthopaedic Surgeons 67th Annual Meeting, Orlando, FL, Mar. 15-19, 2000.
Nagae et al., "Intervertebral disc Regeneration Using Platelet-Rich Plasma and Biodegradable Gelatin Hydrogel Microsphere", Tissue Engineering 13 (1): 147-158 (2007).
Neisius et al., "Renal Oncocytoma: Diagnostic and Therapeutical Consequences," Urologe Ausgabe A., 32(5):415-419, 1993. (Abstract only.).
NIH (Stem Cells: Scientific Progress and Future Research Directions, Department of Health and Human Services, Chapter 1, pp. 14, Jun. 2001.
Nirschl et al., "Elbow tendinopathy: tennis elbow," Clinics in Sports Medicine, vol. 22(4), pp. 813-836 (Oct. 2003).
Ohman et al. "Cardiac Troponin T Levels for Risk Stratification in Acute Myocardial Ischemia," The New England Journal of Medicine, vol. 335, No. 18, pp. 1333-1341, Oct. 31, 1996.
Okuda et al., "Platelet-Rich Plasma Contains High Levels of Platelet-Derived Growth Factor and Transforming Growht Factorbeta and Modulates the Proliferation of Periodontally Related Cells in Vitro", J. Periodontal. 74: 849-857 (2003).
Okuda, "Application of PRP (Platelet Rich Plasma) to Periodontal Treatment," Dental Outlook, vol. 96, No. 4, pp. 874-875, 2001 with English translation.
Osti et al., "Annular Tears and Disc Degeneration in the Lumbar Spine," The Journal of Bone and Joint Surgery, British Editorial Society of Bone and Joint Surgery, vol. 74-B, pp. 678-682 (1992).
Palatianos, et al., Neutrophil Depletion Reduces Myocardial Reperfusion Morbidity, Annals of Thoracic Surgery, 2004, vol. 77, pp. 956-961.
Pang, et al. "Clinical Implications of Angiogenesis in Cancers," Vascular Health and Risk Management, vol. 2, No. 2, pp. 97-108, 2006. (Abstract only.).
Paques et al., "Effect of Autologous Platelet Concentrate in Surgery for Idiopathic Macular Hole", Ophthalmology 106 (5): 932-938 (1999).
Petrungaro, "Immediate Restoration of Multiple Tooth Implants for Aesthetic Implant Restorations", Implant Dentistry 11 (2) : 118-27 (2002).
Pierce, et al. "Platelet-derived Growth Factor and transforming Growth Factor-β Enhance Tissue Repair Activities by Unique Mechanisms," The Journal of Cell Biology, vol. 109, pp. 429-440, 1989.
Playford, et al. "Combined Effect of Coenzyme Q10 and Fenofibrate on Forearm Microcirculatory Function in Type II Diabetes," Artherosclerosis, 168:169-179, 2003.
Price et al., "Local Injection Treatment of Tennis Elbow—Hydrocortisone, Triamcinolone and Lignocaine Compared," British Journal of Rheumatology, vol. 30, pp. 39-44, 1991.
Pruijt, et al., Neutrophils are Indispensable for Hematopoietic Stem Cell Mobilization Induced by Interleukin-8 in Mice, PNAS, Apr. 30, 2002, vol. 9, Issue 9, pp. 6228-6233.
Racz, et al., Buffy Coat or Platelet-rich Plasma?, Vox Sang, 1984, vol. 47, pp. 108-113.
Ramos-Casals et al., "Targeted Therapy for System Sclerosis: how close are we?", Nature Reviews. Rheumatology 6 (5) : 269-278 (2010), abstract only.
Rashidi et al., Does Absolute Neutrophilia Predict Early Congestive Heart Failure After Acute Myocardial Infarction? A Cross-Sectional Study, Southern Medical Journal 101(1):19-23, Jan. 2008.
Regenerative Injections: Prolotherapy, PRP and Stem Cell; Rejuv Medical; Feb. 1, 2001.
Rink, "Cytosolic Calcium in Platelet Activation," Cellular and Molecular Life Sciences, vol. 44, No. 2, pp. 97-100, downloaded from http://www.springerlink.com/content/j41h051h8866m352/?target=print, Abstract only, Feb. 1988.
Roberts et al., "Relation between infarct size and ventricular arrhythmia," British Heart Journal, vol. 37, pp. 1169-1175 (1975).

(56) References Cited

OTHER PUBLICATIONS

Sawamura et al., "Characterization of in Vivo Effects of Platelet-Rich Plasma and Biodegradable Gelatin Hydrogel Microspheres on Degenerated Intervertebral Discs", Tissue engineering: Part A 15 (12): 3719-3727 (2009).
Schroeder et al., "Proliferation of Annulus Fibrosus Cells in Platelet Rich Plasma—a Natural 3D Scaffold: An in Vitro Study: Gp8," Spine Journal Meeting Abstracts, Spine: Affiliated Society Meeting Abstracts. Supplement 2011 ISSLS Society Meeting Abstracts:page #] (Abstract) (Oct. 2011).
Sharpe, P.T., Chapter 5, Centrifugal Elutriation, R.H. Burdon and P.H. van Knippenberg editors, Laboratory Techniques in Biochemistry and Molecular Biology, Elsevier Science Publishers, Amsterdam, NL, pp. 91-94, 97-100, 101 and 105, 1998.
Shigenobu, "Effects of Platelet-Derived Growth Factor on Lacerated Tendons," Medical Magazine of Hiroshima University, vol. 48, No. 1, pp. 1-16, 2000.
Shim et al. "Stem Cell Cardiomyoplasty: State-of-the-Art," Annals of the Academy of Medicine, Singapore, vol. 33, No. 4, pp. 451-460, 2004.
Shvets, "Local Injections of Anesthetics and Corticosteroids in the Treatment of Degenerative Changes in the Spine," Chirugia narzadow ruchu i ortopedia polska, 45(3):259-63, 1980. (Abstract only.).
Snyder et al., "Calcium-Dependent Proteolysis of Actin During Storage of Platelet Concentrates," Blood, vol. 73, No. 5, pp. 1380-1385, 1989.
Snyder et al., "Topical platelet growth factor therapy: of lotions and potions," Transfusion, vol. 41, pp. 1186-1189 (Oct. 2001).
Tang, et al., "The Effects of pCO2 and pH on Platelet Shape Change and Aggregation for Human and Rabbit Platelet-Rich Plasma," Thrombosis Research, vol. 10, No. 1, pp. 135-146, 1977.
Taylor et al., "The Response of Rabbit Patellar Tendons After Autologous Blood Injection," Medicine & Science in Sports & Exercise, vol. 34, No. 1, pp. 70-73, 2002.
Thomson et al. (PNAS, 92:7844-7848 (Aug. 1995).
Valant, et al., Thrombotic Thrombocytopenic Purpura Plasma Enhances Platelet-Leucocyte Interaction in Vitro, British Journal of Haematology, 1998, vol. 100, pp. 24-32.
Valeri et al., Volume of RBCs, 24- and 48-hour posttransfusion survivals and lifespan of 51 Cr and biotin-X-N-hydroxysuccinimide (NHS)-labeled autologous baboon RBCs: effect of the anticoagulant and blood pH on 51 Cr and biotin-X-NHS elution in vivo, Transfusion, 2002, vol. 42, pp. 343-348.
Vasconcelos et al., "Quality of Platelet Concentrates Derived by Platelet Rich Plasma, Buffy Coat and Apheresis," Transfusion and Apheresis Science, vol. 29, No. 1, pp. 13-16, 2003.
Vassallo et al., "A Critical Comparison of Platelet Preparation Methods," Current Opinion in Hematology, vol. 13, pp. 323-330, 2006.
Wang, P.J., Circulation, 2006, vol. 113, p. 2374-2376.
Website download from Medtronic, "Magellan" System Features and Benefits, 3 pages, 2004.
Weibrich et al., "The Harvest Smart 1-3 PReP™ system versus the Friadent-Schutze platelet-rich plasma kit," Clinical Oral Implants Research, vol. 14 (2), pp. 233-239 (Apr. 2003).

What is a Normal Platelet Count?, Datasheet [on line]. WebM D, May 2011 [retrieved on Jan. 15, 2016]. Retrieved from the Internet: <URL: http:/ !answers.webmd.com/answers/1198204/what-is-a-normal-platelet-cou nt>.
White Blood Cell Count, Datasheet [online]. RnCeus, 2013 [retrieved on Jan. 15, 2016]. Retrieved from the Internet: <URL: http://www.rnceus.com/cbc/cbcwbc.html>.
Willems et al., "Prostaglandin 12 (Prostacyclin) Produced by Cultured Human Vascular Endothelial Cells in the Absence of Platelets", J. Molecular Medicine 3 : 195-201 (1978).
www.mahasbtc.aarogya.com/blood-bank/preservation-and-storage, p. 2 only, accessed May 16, 2012.
Yang et al., "Dielectric Properties of Human Leukocyte Subpopulations Determined by Electrorotation as a Cell Separation Criterion," Biophysical Journal, vol. 76, pp. 3307-3314, Jun. 1999.
Yu et al., "A role for T lymphocytes in mediating cardiac diastolic function", Amer J Physiol Heart Circ Physiol, 2005, vol. 289, pp. H643-H651.
Yu et al., "Effects of myocardial platelet rich plasma injection on rats with acute myocardial infarction:(99)Tc(m)-MIBI gated SPECT imaging evaluation results," Chin J Cardiol, vol. 40(5), pp. 392-396 (May 2012).
Yu et al., "Progressive and Regressive Changes in the Nucleus Pulposus. Part II. The Adult," Radiology, vol. 169(1), pp. 93-97 (Oct. 1988).
Zhang et al., "Emergent cardiopulmonary bypass in canines with penetrating cardiac wounds caused by gunshot," Emergency Medical J., vol. 24, pp. 764-768 (2007).
Zimmermann et al., "Different preparation methods to obtain platelet components as a source of growth factors for local application," Transfusion, vol. 41, pp. 1217-1224 (Oct. 2001).
Abi-Younes et al., "The Stromal Cell-Derived Factor-1 Chemokine Is a Potent Platelet Agonist Highly Expressed in Atherosclerotic Plaques," *Circulation Research*, vol. 86, pp. 131-138 (Feb. 4, 2000).
Bahmanpour et al., "Effects of Platelet-Rich Plasma & Platelet-Rich Fibrin with and without Stromal Cell-Derived Factor-1 on Repairing Full-Thickness Cartilage Defects in Knees of Rabbits," *Iran J Med Sci*, vol. 41(6), pp. 507-517 (Nov. 2016).
Kaplan et al., "CD34 expression on platelets," *Platelets*, vol. 14(2), pp. 83-87 (Mar. 2003). (Abstract only).
Kowalska et al., "Stromal cell-derived factor-1 and macrophage-derived chemokine: 2 chemokines that activate platelets," *Blood*, vol. 96(1), pp. 50-57 (Jul. 1, 2000).
Agu et al., "The Lung as a Route for Systemic Delivery of Therepeutic Proteins and Peptides," Respiratory Research, 2001, vol. 2, No. 4, p. 198-209.
Beutler et al., "The definition of anemia: what is the lower limit of normal of the blood hemoglobin concentration?" Blood, 2006, vol. 107, pp. 1747-1750.
Hillyer et al., Blood Banking and Transfusion Medicine, Basic Principles & Practice, Second edition, 2007, Churchill Livingstone, published Oct. 18, 2006, p. 190-194.
Pietramaggiori et al., "Freeze-Dried Platelet-Rich Plasma Shows Beneficial Healing Properties in Chronic Wounds," Wound Repair and Regeneration, 2006, vol. 14, p. 573-580.

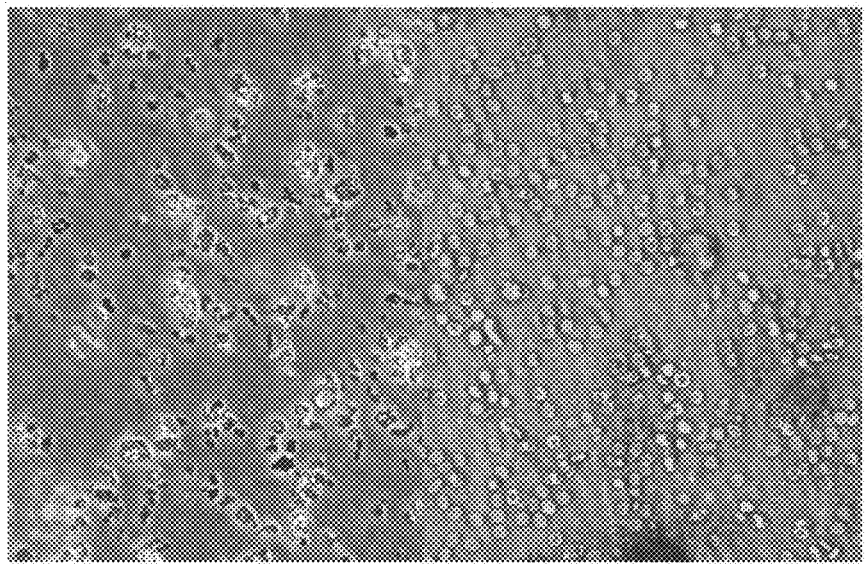
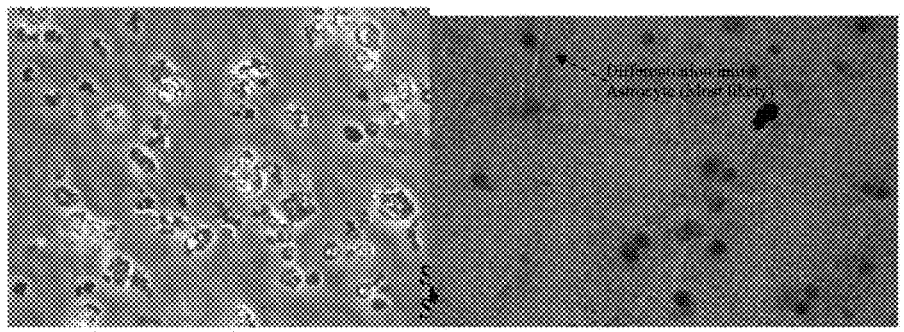

PLATELET-RICH PLASMA COMPOSITIONS AND METHODS OF PREPARATION

RELATED APPLICATIONS

This application is a continuation of U.S. application Ser. No. 14/292,658, filed May 30, 2014 which claims the priority of Provisional Application No. 61/830,754, filed Jun. 4, 2013. Both applications are incorporated herein by reference in their entirety.

BACKGROUND OF THE INVENTION

Field of the Invention

Embodiments of the invention related to platelet-rich plasma (PRP) and platelet compositions and their use.

Description of the Related Art

Cell therapy is rapidly evolving in medicine. A variety of cell lines including embryonic stem cells (ESC), induced pluripotent stem cells (iPSCs), adult stem cells (ASCs) and progenitor cells (PCs) derived from a variety of tissues are being employed in preclinical and now clinical trials to treat disease. A consistent issue with the use of any type of cell line, however, is differentiating it to an appropriate type of cell. These pluripotent or multipotent cells need to be driven to a specific cell line in order for them to be used for a specific disease or disorder.

Specifically, iPSCs can be created by overexpressing key transcriptional factors. Landmark work by Yamanaka and coworkers (U.S. Pat. No. 8,278,104) and others have confirmed that somatic cells can be transformed into pluripotent cells via these methods. Lentiviruses, retroviruses, adenoviruses, plasmids and transposable elements have all been used to create these cells lines. This methodology, however, may result in the integration of viral DNA into the genome.

Cells lines can be differentiated into mature cell types such as a muscle cells, a skin cell or an astrocyte, a mature type of brain cell. A variety of growth factors and other cytokines can be used to push immature cell lines into differentiated cell types.

Unfortunately, "genetic or epigenetic errors may be introduced during nuclear reprogramming, and the generation of tissues from pluripotent stem cells employs laboratory methods for cell generation and expansion that increase the risk of genetic instability, epigenetic modification, and the generation of tumorigenic cells. These issues may be addressed in part by using non-viral reprogramming methods." (Volz et al 2012)

SUMMARY OF THE INVENTION

Blood is comprised of Red Blood Cells (RBC), White Blood Cells (WBC), Plasma, and Platelets. Platelet-rich plasma (PRP) is a fractionation of whole blood containing concentrated platelets and white blood cells and which may include high quantities of cytokines such as vascular endothelial growth factor (VEGF), transforming growth factor beta (TGF-β), and platelet-derived growth factor (PDGF). Platelets are responsible for blood clotting and when activated, release growth factors and other bioactive molecules which are involved in stimulating the healing of bone and soft tissue. For example, platelets release VEGF and basic fibroblast growth factor from alpha granules and adenosine diphosphate (ADP), adenosine triphosphate (ATP), and ionized calcium from dense granules. White blood cells (WBCs), also known as leukocytes, are involved in defending the body against both infectious disease and foreign materials. The two most common types of white blood cells are the lymphocytes and neutrophils. Lymphocytes secrete factors, lymphokines, which modulate the functional activities of many other types of cells and are often present at sites of chronic inflammation. Neutrophils, which are the most abundant white blood cell type in mammals, are recruited to the site of injury within minutes following trauma. Neutrophils form an essential part of the innate immune system, playing a role in inflammation.

Platelet-rich plasma (PRP) is a bioactive fraction of whole blood that has been used to treat a variety of connective tissue disorders including chronic tennis elbow. Within PRP are dozens of molecules that could be used to help differentiate cell lines. By using an autologous fraction of whole blood to create PRP, a viral free method of differentiating cells is provided. A specific example is given where a dedifferentiated cell line is shown to differentiate into a specific type of cell. The compositions and methods herein described do not limit the invention to this cell line but it should be realized that the methods and compositions could be used in variety of cell lines including but not limited to ESC, iPSCs, ASCs (derived from any source) and any line of progenitor cells. Furthermore, platelet-rich plasma may be used to create these lines by isolating the appropriate factors and then using these factors to reprogram mature cells into pluripotent cells. These cells could then be differentiated with a different set of factors within the PRP to achieve the desired cell line. This invention would eliminate the need for viral derived vectors or other methods of artificially stimulating nuclear reprogramming or differentiation. Importantly, the use of PRP would enhance the yield of any reprogramming or differentiation method. Imbedded in this invention are novel compositions and methods including specific fractions of whole blood containing platelets, white blood cells, stem cells and specific growth factors. Methods for using these compositions for small molecule or drug discovery are also disclosed. After using PRP to differentiate cell lines, PRP may also be used in combination with these lines therapeutically. PRP may further be used in combination with a genetically engineered small molecule or drug to enhance the effects of PRP or the small molecule. Therapeutic applications include but are not limited to neurologic, cardiac, cardiovascular, peripheral vascular, neoplastic, musculoskeletal, metabolic, inflammatory, infectious, urologic, gynecologic, dermatologic (including cosmetic issues such as wrinkles and baldness), allergic or immunologic, ophthalmologic, obstetric, pediatric, surgical, internal medicine or orthopedic applications. Treatment of specific problems include but are not limited to cartilage degeneration in any joint (knee, hip, shoulder, spine), tendinopathy, bone related problems, cardiovascular injuries and disorders such as acute or chronic heart failure, an acute heart attack and peripheral vascular disease. For clarification, the compositions and methods in this disclosure are examples and are meant to be inclusive of other problems and disorders.

In accordance with one aspect, a method of producing induced pluripotent stem (iPS) cells comprising obtaining fibroblast cells from skin tissue from an individual, administering a growth factor selected from the group consisting of vascular endothelial growth factor (VEGF), granulocyte colony stimulating factor (G-CSF), plerixafor, sargramostim, γ-tocotrienol, vitamin E, ancestim and bone morphogenic growth factor to the individual, isolating platelet-rich plasma (PRP) from whole blood of the individual, and treating the fibroblast cells of the individual with the isolated PRP. In some embodiments, the method wherein the whole blood is obtained from spleen or bone marrow. In some embodiments, the method wherein the platelet-rich plasma comprises a platelet concentration of 151,000/microliter to 7,000,000/microliter or higher, and further comprising treating the fibroblast cells of the individual with a bone marrow concentrate and fraction of adipose tissue. In some embodiments, the method wherein the platelet-rich plasma comprises a platelet concentration of 151,000/microliter to 7,000,000/microliter or higher, and further comprising CD34+ cells at a concentration $1-3 \times 10^9$ per liter to $100 \times 10^9$ per liter or higher. In some embodiments, the method wherein the platelet-rich plasma comprises a platelets in a concentration of 151,000/microliter to 7,000,000/microliter or higher, and further comprising stromal-derived factor-1 (SDF-1) in a concentration of 100 pg/ml to 5000 pg/ml. In some embodiments, the method further comprising measuring the potency of platelet rich plasma by visually observing it over time by at least one method selected from the group consisting of cellular movement, microfluidics, and chemotaxis. In some embodiments, the method wherein the PRP is used in drug discovery to identify new targets. In some embodiments, the method wherein the PRP is used for nuclear reprogramming, cell proliferation, or differentiation. In some embodiments, the method further comprising administrating granulocyte colony-stimulating factor (G-CSF) or any other molecule that stimulates the production of stem cells by the body prior to the preparation of platelet-rich plasma from any source.

In accordance with another aspect, a composition comprising cells from an individual, and platelet-rich plasma (PRP) isolated from whole blood of the individual, wherein the cells of the individual are treated with the PRP to produce induced pluripotent stem (iPS) cells. In some embodiments, the composition wherein the cells are fibroblast cells from skin tissue from the individual. In some embodiments, the composition further comprising a growth factor selected from the group consisting of vascular endothelial growth factor (VEGF), granulocyte colony stimulating factor (G-CSF), plerixafor, sargramostim, γ-tocotrienol, vitamin E, ancestim and bone morphogenic growth factor to the individual. In some embodiments, the composition wherein the whole blood is obtained from spleen or bone marrow. In some embodiments, the composition wherein the composition comprises the platelet-rich plasma comprising a platelets concentration of 151,000/microliter to 7,000,000/microliter or higher and comprises at least one cell selected from the group consisting of embryonic stem cells, induced pluripotent stem cells, adult stem cells, and progenitor cell lines. In some embodiments, the composition wherein the adult stem cells comprise mesenchymal stem cells. In some embodiments, the composition wherein the composition comprises a platelet-rich plasma comprising a platelet concentration of 151,000/microliter to 7,000,000/microliter or higher and comprises progenitor or precursor stem cell lines. In some embodiments, the composition wherein the progenitor or precursor stem cell lines comprise mesenchymal stem precursor lines. In some embodiments, the composition wherein the composition comprises a platelet-rich plasma comprising a platelet concentration of 151,000/microliter to 7,000,000/microliter or higher and comprises CD34+ cells at a concentration $1-3 \times 10^9$ per liter to $100 \times 10^9$ per liter or higher. In some embodiments, the composition wherein the composition comprises a platelet-rich plasma comprising a platelets in a concentration of 151,000/microliter to 7,000,000/microliter or higher and comprises stromal-derived factor-1 (SDF-1) in a concentration of 100 pg/ml to 5000 pg/ml.

In accordance with another aspect, the composition of platelet rich plasma comprising the platelet rich plasma derived from induced pluripotent stem cells at a platelet concentration of 151,000/microliter to 7,000,000/microliter or higher and pluripotent stem cells in any concentration or form. In accordance with another aspect, the method of preparing platelet rich plasma and storing it in a reduced and or increased oxygen concentration device.

BRIEF DESCRIPTION OF THE DRAWINGS

These and other feature of this invention will now be described with reference to the drawings of preferred embodiments which are intended to illustrate and not to limit the invention.

FIG. 1 shows Glioblastoma cells (012705) cultured with (right panels) and without (left panels) 10% PRP for 10 days at 100× and 200× magnification.

DETAILED DESCRIPTION OF THE PREFERRED EMBODIMENT

Platelet-Rich Plasma Preparation and Compositions

The term "platelet-rich plasma" or "PRP" as used herein is a broad term which is used in its ordinary sense and is a concentration of platelets greater than the peripheral blood concentration suspended in a solution of plasma, or other excipient suitable for administration to a human or non-human animal including, but not limited to isotonic sodium chloride solution, physiological saline, normal saline, dextrose 5% in water, dextrose 10% in water, Ringer solution, lactated Ringer solution, Ringer lactate, Ringer lactate solution, and the like. PRP compositions may be an autologous preparation from whole blood taken from the subject to be treated or, alternatively, PRP compositions may be prepared from a whole blood sample taken from a single donor source or from whole blood samples taken from multiple donor sources. In general, PRP compositions comprise platelets at a platelet concentration that is higher than the baseline concentration of the platelets in whole blood. In some embodiments, PRP compositions may further comprises WBCs at a WBC concentration that is higher than the baseline concentration of the WBCs in whole blood. As used herein, baseline concentration means the concentration of the specified cell type found in the patient's blood which would be the same as the concentration of that cell type found in a blood sample from that patient without manipulation of the sample by laboratory techniques such as cell sorting, centrifugation or filtration. Where blood samples are obtained from more than one source, baseline concentration means the concentration found in the mixed blood sample from which the PRP is derived without manipulation of the mixed sample by laboratory techniques such as cell sorting, centrifugation or filtration.

In some embodiments, PRP compositions comprise elevated concentrations of platelets and WBCs and lower levels of RBCs and hemoglobin relative to their baseline concentrations. In some embodiments of PRP composition, only the concentration of platelets is elevated relative to the baseline concentration. Some embodiments of PRP composition comprise elevated levels of platelets and WBCs compared to baseline concentrations. In some embodiments, PRP compositions comprise elevated concentrations of platelets and lower levels of neutrophils relative to their baseline concentrations. Some embodiments of PRP composition comprise elevated levels of platelets and neutrophil-depleted WBCs compared to their baseline concentrations.

In some embodiments of PRP, the ratio of lymphocytes and monocytes to neutrophils is significantly higher than the ratios of their baseline concentrations.

The PRP formulation may include platelets at a level of between about 1.01 and about 2 times the baseline, about 2 and about 3 times the baseline, about 3 and about 4 times the baseline, about 4 and about 5 times the baseline, about 5 and about 6 times the baseline, about 6 and about 7 times the baseline, about 7 and about 8 times the baseline, about 8 and about 9 times the baseline, about 9 and about 10 times the baseline, about 11 and about 12 times the baseline, about 12 and about 13 times the baseline, about 13 and about 14 times the baseline, or higher. In some embodiments, the platelet concentration may be between about 4 and about 6 times the baseline. Typically, a microliter of whole blood comprises at least 140,000 to 150,000 platelets and up to 400,000 to 500,000 platelets. The PRP compositions may comprise about 500,000 to about 7,000,000 platelets per microliter. In some instances, the PRP compositions may comprise about 500,000 to about 700,000, about 700,000 to about 900,000, about 900,000 to about 1,000,000, about 1,000,000 to about 1,250,000, about 1,250,000 to about 1,500,000, about 1,500,000 to about 2,500,000, about 2,500,000 to about 5,000,000, or about 5,000,000 to about 7,000,000 platelets per microliter.

The WBC concentration is typically elevated in PRP compositions. For example, the WBC concentration may be between about 1.01 and about 2 times the baseline, about 2 and about 3 times the baseline, about 3 and about 4 times the baseline, about 4 and about 5 times the baseline, about 5 and about 6 times the baseline, about 6 and about 7 times the baseline, about 7 and about 8 times the baseline, about 8 and about 9 times the baseline, about 9 and about 10 times the baseline, or higher. The WBC count in a microliter of whole blood is typically at least 4,100 to 4,500 and up to 10,900 to 11,000. The WBC count in a microliter of the PRP composition may be between about 8,000 and about 10,000; about 10,000 and about 15,000; about 15,000 and about 20,000; about 20,000 and about 30,000; about 30,000 and about 50,000; about 50,000 and about 75,000; and about 75,000 and about 100,000.

Among the WBCs in the PRP composition, the concentrations may vary by the cell type but, generally, each may be elevated. In some variations, the PRP composition may comprise specific concentrations of various types of white blood cells. The relative concentrations of one cell type to another cell type in a PRP composition may be the same or different than the relative concentration of the cell types in whole blood. For example, the concentrations of lymphocytes and/or monocytes may be between about 1.1 and about 2 times baseline, about 2 and about 4 times baseline, about 4 and about 6 times baseline, about 6 and about 8 times baseline, or higher. In some variations, the concentrations of the lymphocytes and/or the monocytes may be less than the baseline concentration. The concentrations of eosinophils in the PRP composition may be less than baseline, about 1.5 times baseline, about 2 times baseline, about 3 times baseline, about 5 times baseline, or higher.

In whole blood, the lymphocyte count is typically between 1,300 and 4,000 cells per microliter, but in other examples, the lymphocyte concentration may be between about 5,000 and about 20,000 per microliter. In some instances, the lymphocyte concentration may be less than 5,000 per microliter or greater than 20,000 per microliter. The monocyte count in a microliter of whole blood is typically between 200 and 800. In the PRP composition, the monocyte concentration may be less than about 1,000 per microliter, between about 1,000 and about 5,000 per microliter, or greater than about 5,000 per microliter. The eosinophil concentration may be between about 200 and about 1,000 per microliter elevated from about 40 to 400 in whole blood. In some variations, the eosinophil concentration may be less than about 200 per microliter or greater than about 1,000 per microliter.

In certain variations, the PRP composition may contain a specific concentration of neutrophils. The neutrophil concentration may vary between less than the baseline concentration of neutrophils to eight times than the baseline concentration of neutrophils. In some embodiments, the PRP composition may include neutrophils at a concentration of 50-70%, 30-50%, 10-30%, 5-10%, 1-5%, 0.5-1%, 0.1-0.5% of levels of neutrophils found in whole blood or even less. In some embodiments, neutrophil levels are depleted to 1% or less than that found in whole blood. In some variations, the neutrophil concentration may be between about 0.01 and about 0.1 times baseline, about 0.1 and about 0.5 times baseline, about 0.5 and 1.0 times baseline, about 1.0 and about 2 times baseline, about 2 and about 4 times baseline, about 4 and about 6 times baseline, about 6 and about 8 times baseline, or higher. The neutrophil concentration may additionally or alternatively be specified relative to the concentration of the lymphocytes and/or the monocytes. One microliter of whole blood typically comprises 2,000 to 7,500 neutrophils. In some variations, the PRP composition may comprise neutrophils at a concentration of less than about 1,000 per microliter, about 1,000 to about 5,000 per microliter, about 5,000 to about 20,000 per microliter, about 20,000 to about 40,000 per microliter, or about 40,000 to about 60,000 per microliter. In some embodiments, neutrophils are eliminated or substantially eliminated. Means to deplete blood products, such as PRP, of neutrophils is known and discussed in U.S. Pat. No. 7,462,268, which is incorporated herein by reference.

Several embodiments are directed to PRP compositions in which levels of platelets and white blood cells are elevated compared to whole blood and in which the ratio of monocytes and/or lymphocytes to neutrophils is higher than in whole blood. The ratio of monocytes and/or lymphocytes to neutrophils may serve as an index to determine if a PRP formulation may be efficaciously used as a treatment for a particular disease or condition. PRP compositions where the ratio of monocytes and/or lymphocytes to neutrophils is increased may be generated by either lowering neutrophils levels, or by maintaining neutrophil levels while increasing levels of monocytes and/or lymphocytes. Several embodiments relate to a PRP formulation that contains 1.01 times, or higher, baseline platelets in combination with a 1.01 times, or higher, baseline white blood cells with the neutrophil component depleted at least 1% from baseline.

In some embodiments, the PRP compositions may comprise a lower concentration of red blood cells (RBCs) and/or hemoglobin than the concentration in whole blood. The RBC concentration may be between about 0.01 and about 0.1 times baseline, about 0.1 and about 0.25 times baseline, about 0.25 and about 0.5 times baseline, or about 0.5 and about 0.9 times baseline. The hemoglobin concentration may be depressed and in some variations may be about 1 g/dl or less, between about 1 g/dl and about 5 g/dl, about 5 g/dl and about 10 g/dl, about 10 g/dl and about 15 g/dl, or about 15 g/dl and about 20 g/dl. Typically, whole blood drawn from a male patient may have an RBC count of at least 4,300,000 to 4,500,000 and up to 5,900,000 to 6,200,000 per microliter while whole blood from a female patient may have an RBC count of at least 3,500,000 to 3,800,000 and up to 5,500,000 to 5,800,000 per microliter. These RBC counts generally correspond to hemoglobin levels of at least 132 g/L to 135 g/L and up to 162 g/L to 175 g/L for men and at least 115 g/L to 120 g/L and up to 152 g/L to 160 g/L for women.

In some embodiments, PRP compositions contain increased concentrations of growth factors and other cytokines. In several embodiments, PRP compositions may include increased concentrations of one or more of: platelet-derived growth factor, transforming growth factor beta, fibroblast growth factor, insulin-like growth factor, insulin-like growth factor 2, vascular endothelial growth factor, epidermal growth factor, interleukin-8, keratinocyte growth factor, and connective tissue growth factor. In some embodiments, the platelets collected in PRP are activated by thrombin and calcium chloride to induce the release of these growth factors from alpha granules.

In some embodiments, a PRP composition is activated exogenously with thrombin and/or calcium to produce a gel that can be applied to an area to be treated. The process of exogenous activation, however, results in immediate release of growth factors. Other embodiments relate to activation of PRP via in vivo contact with collagen containing tissue at the treatment site. The in vivo activation of PRP results in slower growth factor release at the desired site.

Methods of Making

The PRP composition may comprise a PRP derived from a human or animal source of whole blood. The PRP may be prepared from an autologous source, an allogenic source, a single source, or a pooled source of platelets and/or plasma. To derive the PRP, whole blood may be collected, for example, using a blood collection syringe. The amount of blood collected may depend on a number of factors, including, for example, the amount of PRP desired, the health of the patient, the severity or location of the tissue damage and/or the MI, the availability of prepared PRP, or any suitable combination of factors. Any suitable amount of blood may be collected. For example, about 1 cc to about 150 cc of blood or more may be drawn. More specifically, about 27 cc to about 110 cc or about 27 cc to about 55 cc of blood may be withdrawn. In some embodiments, the blood may be collected from a patient who may be presently suffering, or who has previously suffered from, connective tissue damage and/or an MI. PRP made from a patient's own blood may significantly reduce the risk of adverse reactions or infection.

In an exemplary embodiment, about 55 cc of blood may be withdrawn into a 60 cc syringe (or another suitable syringe) that contains about 5 cc of an anticoagulant, such as a citrate dextrose solution. The syringe may be attached to an apheresis needle, and primed with the anticoagulant. Blood (about 27 cc to about 55 cc) may be drawn from the patient using standard aseptic practice. In some embodiments, a local anesthetic such as anbesol, benzocaine, lidocaine, procaine, bupivicaine, or any appropriate anesthetic known in the art may be used to anesthetize the insertion area.

The PRP may be prepared in any suitable way. For example, the PRP may be prepared from whole blood using a centrifuge. The whole blood may or may not be cooled after being collected. Isolation of platelets from whole blood depends upon the density difference between platelets and red blood cells. The platelets and white blood cells are concentrated in the layer (i.e., the "buffy coat") between the platelet depleted plasma (top layer) and red blood cells (bottom layer). For example, a bottom buoy and a top buoy may be used to trap the platelet-rich layer between the upper and lower phase. This platelet-rich layer may then be withdrawn using a syringe or pipette. Generally, at least 60% or at least 80% of the available platelets within the blood sample can be captured. These platelets may be resuspended in a volume that may be about 3% to about 20% or about 5% to about 10% of the sample volume.

In some examples, the blood may then be centrifuged using a gravitational platelet system, such as the Cell Factor Technologies GPS System® centrifuge. The blood-filled syringe containing between about 20 cc to about 150 cc of blood (e.g., about 55 cc of blood) and about 5 cc citrate dextrose may be slowly transferred to a disposable separation tube which may be loaded into a port on the GPS centrifuge. The sample may be capped and placed into the centrifuge. The centrifuge may be counterbalanced with about 60 cc sterile saline, placed into the opposite side of the centrifuge. Alternatively, if two samples are prepared, two GPS disposable tubes may be filled with equal amounts of blood and citrate dextrose. The samples may then be spun to separate platelets from blood and plasma. The samples may be spun at about 2000 rpm to about 5000 rpm for about 5 minutes to about 30 minutes. For example, centrifugation may be performed at 3200 rpm for extraction from a side of the separation tube and then isolated platelets may be suspended in about 3 cc to about 5 cc of plasma by agitation. The PRP may then be extracted from a side port using, for example, a 10 cc syringe. If about 55 cc of blood may be collected from a patient, about 5 cc of PRP may be obtained.

As the PRP composition comprises activated platelets, active agents within the platelets are released. These agents include, but are not limited to, cytokines (e.g., IL-1B, IL-6, TNF-A), chemokines (e.g., ENA-78 (CXCL5), IL-8 (CXCL8), MCP-3 (CCL7), MIP-1A (CCL3), NAP-2 (CXCL7), PF4 (CXCL4), RANTES (CCLS)), inflammatory mediators (e.g., PGE2), and growth factors (e.g., Angiopoitin-1, bFGF, EGF, FGF, HGF, IGF-I, IGF-II, PDAF, PDEGF, PDGF AA and BB, TGF-.beta. 1, 2, and 3, and VEGF).

The PRP composition may be delivered as a liquid, a solid, a semi-solid (e.g., a gel), an inhalable powder, or some combination thereof. When the PRP is delivered as a liquid, it may comprise a solution, an emulsion, a suspension, etc. A PRP semi-solid or gel may be prepared by adding a clotting agent (e.g., thrombin, epinephrine, calcium salts) to the PRP. The gel may be more viscous than a solution and therefore may better preserve its position once it is delivered to target tissue. In some embodiments, the delivery to the target tissue can include delivery to a treatment area in the body as well as incorporation into cell cultures or suspensions as described herein. In some embodiments, the PRP composition is delivered without a clotting agent.

In some instances, it may be desirable to deliver the PRP composition as a liquid and have it gel or harden in situ. For example, the PRP compositions may include, for example, collagen, cyanoacrylate, adhesives that cure upon injection into tissue, liquids that solidify or gel after injection into tissue, suture material, agar, gelatin, light-activated dental composite, other dental composites, silk-elastin polymers, Matrigel® gelatinous protein mixture (BD Biosciences), hydrogels and/or other suitable biopolymers. Alternatively, the above mentioned agents need not form part of the PRP mixture. For example, the above mentioned agents may be delivered to the target tissue before or after the PRP has been delivered to the target tissue to cause the PRP to gel. In some embodiments, the PRP composition may harden or gel in response to one or more environmental or chemical factors such as temperature, pH, proteins, etc.

The PRP may be buffered using an alkaline buffering agent to a physiological pH. The buffering agent may be a biocompatible buffer such as HEPES, TRIS, monobasic phosphate, monobasic bicarbonate, or any suitable combination thereof that may be capable of adjusting the PRP to physiological pH between about 6.5 and about 8.0. In certain embodiments, the physiological pH may be from about 7.3 to about 7.5, and may be about 7.4. For example, the buffering agent may be an 8.4% sodium bicarbonate solution. In these embodiments, for each cc of PRP isolated from whole blood, 0.05 cc of 8.4% sodium bicarbonate may be added. In some embodiments, the syringe may be gently shaken to mix the PRP and bicarbonate.

As noted above, the PRP composition may comprise one or more additional agents, diluents, solvents, or other ingredients. Examples of the additional agents include, but are not limited to, thrombin, epinephrine, collagen, calcium salts, pH adjusting agents, materials to promote degranulation or preserve platelets, additional growth factors or growth factor inhibitors, NSAIDS, steroids, anti-infective agents, and mixtures and combinations of the foregoing.

In some embodiments, the PRP compositions may comprise a contrast agent for detection by an imaging technique such as X-rays, magnetic resonance imaging (MRI), or ultrasound. Examples of such contrast agents include, but are not limited to, X-ray contrast (e.g., IsoVue), MRI contrast (e.g., gadolinium), and ultrasound contrast.

The PRP composition may be modified using a filtration device and/or cell sorter. The filtration device may use vacuum and/or gravity to remove a portion of the platelet, WBCs, and/or RBCs. In some variations, a cell sorter may receive a CBC input from an automated blood analyzer and/or a gene chip reader. A user may select or confirm one or more modifications to be made to the PRP composition. Of course, the cell sorter may be used with whole blood, portions of whole blood, and/or PRP. The cell sorter may sort the PRP composition based on electric charge, density, size, deformation, fluorescence, or the like. Examples of cell sorters include the BD FACSAria® cell sorter, the Cytopeia InFlux® cell sorter, those manufactured by Beckman Coulter, the Cytonome Gigasort® cell sorter, and the like.

PRP Compositions According to Embodiments of the Invention

PRP is prepared by any method including but not limited to cell sorting, centrifugation, gravity filtration or other methods. The composition described herein can be created by a cell sorter device that uses electric charge, density, size, deformation, fluorescence or other means to achieve the composition. As part of this invention a variety of methods and compositions are claimed as novel.

Granulocyte-colony stimulating factor (GCSF) can mobilize cells from bone marrow including platelets. Pretreating patients with GCSF will enhance the value of PRP by increasing the number of platelets and other reparative cells. This may be especially true in patients with low platelet counts or in older patients that have lower cell counts. GCSF or other molecules that mobilize cells are given once, twice or many times prior to drawing whole blood from any source as described above. A preferred protocol would be to give GCSF for several days prior to the PRP isolation.

One specific method is to administer granulocyte colony-stimulating factor (G-CSF, also known as pegfilgrastim) or any other molecule that stimulates the production of stem cells by the body to a patient prior to the preparation of PRP. 5-50 micrograms per kilogram per day is administered to a patient for 1-10 days. PRP is then prepared from whole blood of the patient. The whole blood may be from any source including bone marrow and spleen. In a preferred embodiment, 10 micrograms per kilogram per day of G-CSF is administered subcutaneously to a patient for 1-10 days. PRP is then prepared from whole blood of the patient from any source including bone marrow or the spleen. Additional medications or newer molecules that stimulate blood or stem cell production could be added or substituted. Embodiments of the invention are directed to the use of a molecule to stimulate endogenous production of desired cells prior to preparing the PRP or bone marrow concentrate to be used therapeutically or for the reprogramming, proliferation, or differentiation of cells. Examples of other potential molecules include but are not limited to: plerixafor, sargramostim, gamma-tocotrienol, vitamin E and ancestim. As science evolves, newer molecules that help mobilize desired cells will be developed. It is anticipated by this filing that these newer molecules would be included in the list that could be administered prior to the production of PRP or other bioactive blood fractions.

By giving a patient such a mobilizing drug prior to preparing PRP, it should be noted that the composition will change compared to without such a cell mobilization drug. Therefore, a variety of compositions are claimed to be novel and useful.

In alternate embodiments, the molecule, such as G-CSF is administered at the same time that the PRP is administered or the molecule, such as G-CSF, is administered after the administration of PRP for a period to be determined depending on the treatment. For example, for treatment of a connective tissue injury, G-CSF with or without PRP may be administered over a period of weeks of months on a regular basis such as once a week, twice a week, three times per week or more as determined by the medical practitioner. In some embodiments, the molecule, such as G-CSF is administered before blood is taken from the patient for isolation of PRP for a period of 1-10 days as well as at the same time as administration of PRP to the patient and/or after administration of PRP as described above. PRP contains cytokines such as SDF-1 that are chemoattractive for stem cells. In some embodiments, the use of GCSF would enhance the value of the PRP treatment by mobilizing more cells.

In some embodiments, the PRP could also be used in combination with other drugs or fillers such as calcium phosphate, collagen or even with botox.

Embodiments of the invention are directed to mobilizing cells from bone marrow using GCSF or other similar type molecules prior to the production of PRP of any type.

Methods of Use

Embodiments of the invention are directed to the use of that PRP for a variety of research and clinically applications including but not limited to:

Cell culture of any type.

Connective Tissue Disorders of any type including but not limited to: tennis elbow, carpal tunnel syndrome, deQuervain's tenosynovitis, medial epicondylitis, ulnar collateral ligament injuries of the elbow, cartilage injuries of any type, cartilage degeneration of any type or location, rotator cuff disease including partial and complete tears, labral tears, biceps tendon disorders, fractures of any type, cervical radiculopathy, acute or chronic spinal cord injuries, disc herniations, disc degeneration, spinal disorders of any type including spinal stenosis and facet arthropathy, acute bony injuries including subchondral edema, tendinopathy of any type including gluteal, quadriceps, patellar, achilles and others, osteoarthritis of any joint, rheumatoid arthritis, arthritis of any type, achilles tendon tears, muscle injuries of any type or severity, or any other musculoskeletal injury or disorder.

Cardiovascular disorders of any type including but not limited to: acute myocardial infarction, acute or chronic heart failure and peripheral vascular disease of any grade.

Neurologic injuries or disorders of any type including Parkinson's disease, brain cancer or Alzheimer's disease.

Wound healing. The methods outlined above could be used to specifically treat acute or chronic wounds.

Infections of any type.

Dermatologic or Cosmetic Injuries or disorders such baldness, wrinkles, burns or even skin cancer.

Internal organ injuries or disorders such as diabetes, hernias or fistulas.

It should be recognized that the concept is to give a cell mobilization agent either before, during, and/or after preparing and using PRP as a treatment for any medical issue in humans or animals.

The PRP composition may be delivered at any suitable dose. In some embodiments, the dose may be between about 1 cc and about 3 cc, between about 3 cc and about 5 cc, between about 5 cc and about 10 cc, between about 10 cc and about 20 cc, or more. The dose may be delivered according to a medical procedure (e.g., at specific points in a procedure) and/or according to a schedule. For example, prior to an elective cardioversion, the PRP composition may be delivered about 24 hours, about 12 hours, about 6 hours, about 2 hours, and/or about 1 hour before the procedure begins.

In some embodiments, the PRP composition may be delivered to tissue damaged by ischemia or reperfusion injury. The list of tissues includes, but is not limited to, the heart, ischemic limbs, ischemic or damaged organs including the brain and skin. The PRP composition may be delivered to an individual in need thereof by injection using a syringe or catheter. The PRP composition may also be delivered via delivery device such as a dermal patch, a spray device, sutures, stents, screws, plates, or some other implantable medical device such as bioresorbable tissue patch. The PRP composition may be used as a coating or incorporated into the delivery device. The PRP delivery device may be incubated with PRP prior to use. Incubation times may be from a few seconds up to any convenient time such as a few seconds to hours before use, such as less than 1 minute, 5-10 minutes, 10 minutes to an hour, 1-3 hours, 4-12 hours, 13-24 hours, 1-3 days, or 3-31 days. PRP compositions may be used in conjunction with an ointment, bone graft, or drug.

The PRP alone or in combination with a delivery device may be conveniently stored in an appropriate chamber. In some embodiments, the PRP and/or PRP combined delivery device may be stored frozen and/or under reduced oxygen concentration or increased oxygen concentration, low and/or high pH, low and/or high pressure, low and/or high UV or other light conditions, low and/or high temperature. Storage times may vary from such as less than 1 minute, 5-10 minutes, 10 minutes to an hour, 1-3 hours, 4-12 hours, 13-24 hours, 1-3 days, 3-31 days, or 1-12 months or 1-5 years. The PRP composition alone or in combination with the delivery device may then be used clinically as appropriate.

In one exemplary embodiment, a platelet rich plasma composition is prepared and combined with a stent in an appropriate low oxygen chamber for 1-30 minutes, preferably about 10 minutes. The chamber is then exposed to ultraviolet light for a brief period of time, such as 1-60 seconds, 1-5 minutes, or 5-15 minutes. The stent is then removed from the chamber and implanted into a patient. It is expected that this chamber will improve the biologic activity of the platelet rich plasma and or device.

The site of delivery of the PRP composition is typically at or near the site of tissue damage. The site of tissue damage may be determined by well-established methods including imaging studies and patient feedback or a combination thereof. The preferred imaging method used may be determined based on the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging NOGA mapping and ultrasound techniques. The patient may also assist in locating the site of tissue injury or damage by pointing out areas of particular pain and/or discomfort.

The PRP compositions described herein may also be used to treat peripheral vascular disease, strokes or other ischemic areas such as a kidney that was damaged. PRP compositions could also be used as a primary or secondary treatment for pulmonary disease.

In some examples, a PRP composition may be used to treat a patient diagnosed with an acute myocardial infarction or ischemic heart disease. Treatment with the PRP composition may occur in the field or in the emergency room setting. Criteria for PRP composition treatment may include positive cardiac markers, ST-elevations, or new wall motion abnormalities identified on echocardiogram, for example. The decision to treat with a PRP composition, and the treatment location(s), may depend upon one or more characteristics of the myocardial infarction. For example, a myocardial infarction may be characterized as a ST-elevation myocardial infarction (STEMI) or non-ST-elevation myocardial infarction (NSTEMI), a Q-wave or non-Q-wave myocardial infarction, and whether they are subendocardial or transmural. Myocardial infarctions may also be characterized anatomically by cardiac wall region and/or the suspected blockage site in the cardiac vasculature. Myocardial infarctions may also be characterized as anterior, lateral, inferior, posterior, septal, or right-ventricular in location, and may involve disease or blockage of the left-anterior descending, left circumflex, left main, posterior-descending and right coronary arteries, for example.

In some embodiments, timing of the PRP preparation and application may be based upon other treatments that are indicated in a patient with a myocardial infarction or ischemic heart disease. In some embodiments, a PRP composition may be prepared and delivered before, during, and/or after reperfusion therapy is performed to treat an acute myocardial infarction, a previous myocardial infarction, or ischemic heart disease. Reperfusion therapies may include thrombolytic therapy (such as heparin, TPA and or other pharmacologic agents), angioplasty, stenting (including bare metal stents and drug-eluting stents) or coronary artery bypass graft (CABG) surgery. In some instances, reperfusion therapy may be associated with an increased risk of an arrhythmia, including sudden death. Also, it is believed that the etiology of reperfusion arrhythmias or reperfusion arrhythmia risk may be different from the arrhythmia etiologies associated with the myocardial infarction itself. For example, some reperfusion arrhythmias may be caused by triggered activity and/or re-entry. In some embodiments, PRP composition is prepared before or at the start of a reperfusion procedure, but not used unless an arrhythmia occurs during the procedure. In other embodiments, the patient may be prophylactically pre-treated with a PRP composition before reperfusion occurs, e.g., before guidewire passage across an occlusion, stent positioning, stent expansion, or reestablishment of coronary flow through a bypass segment.

In some embodiments, the PRP composition is injected into or near an infarct site. The location of the infarct site may be determined or approximated using various techniques. For example, in some variations, diagnostic procedures such as an electrophysiology study or an electrical mapping study of the heart may be used. In other variations, one or more imaging technologies such as MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), NOGA mapping, laser optical imaging and ultrasound techniques may be used. Other technologies and approaches that may be used include visual inspection during open chest surgical procedures, localized blood flow determinations, local electrical and structural activity, nuclear cardiology, echocardiography, echocardiographic stress test, coronary angiography, magnetic resonance imaging (MRI), computerized tomography (CT) scans, and ventriculography.

PRP compositions that are formulated as gels or other viscous fluids may be difficult to deliver via a needle or syringe. Thus, in variations where the use of a needle or syringe is desirable, a gelling and/or hardening agent may be optionally added to the PRP composition in situ. One or more needles or catheters may be configured to deliver the PRP composition and/or the gelling or hardening agent simultaneously, or substantially simultaneously, to the cardiac tissue. For example, if a needle is used to deliver the PRP composition, the needle may comprise a plurality of lumens through which the PRP composition and the agent separately travel. Alternatively or additionally, separate needles may be used to deliver the components to the tissue at the same time or one after the other.

The PRP composition may be delivered minimally invasively and/or surgically. For example, the PRP composition may be delivered to the heart using a catheter inserted into the patient via the femoral vein or artery, the internal jugular vein or artery, or any other suitable vein or artery. The PRP composition may be delivered along with one or more medical devices, instruments, or agents to treat the MI and/or other cardiac conditions.

To deliver a PRP composition to the ischemic tissue, a physician may use one of a variety of access techniques. These include surgical (e.g., sternotomy, thoracotomy, minithoracotomy, sub-xiphoidal) approaches, endoscopic approaches (e.g., intercostal and transxiphoidal) and percutaneous (e.g., transvascular, endocardial, and pericardial) approaches. Once access has been obtained, the composition may be delivered via epicardial, endocardial, or transvascular approaches. The composition may be delivered to the cardiac wall tissue or cardiac vessels in one or more locations. This includes intra-myocardial, subendocardial, and/or sub-epicardial administration.

Upon gaining access to the ischemic tissues of the heart, the delivery device may be inserted through any appropriate vessel. The distal end of the delivery device may be then placed against the surface of the myocardium and one or more needles may be advanced into tissue. Following delivery of one or more components of the PRP composition, the needles, if any, may be retracted. Mapping or guidance systems that rely upon voltage, ultrasound or pressure in addition to other systems may be used in combination with injection. The delivery device may then be repositioned for additional delivery of one or more components of the composition or may be removed from the patient. Incisions may then be closed using standard techniques.

The delivery system may deliver the components of the PRP composition in a prescribed ratio (e.g., a ratio of the lymphocytes and the neutrophils). The prescribed ratio may be calculated beforehand or determined on an ad hoc basis once delivery begins. To deliver the components in the prescribed ratio, the delivery device may include one or more gears having a corresponding gear ratio, one or more lumens having a proportional lumen size, or any other suitable mechanism. Some delivery devices may include one or more mixing chambers. The multiple components may be delivered using separate delivery devices or may be delivered one after the other using the same delivery device.

The delivery devices may be advanced through a vessel adjacent to the ischemic tissue to be treated. The PRP composition may be injected directly into the ischemic tissue using a needle and/or a needle-tip catheter. The PRP composition may alternatively or additionally be infused into the vessel.

When the PRP compositions are delivered using one or more catheters, any suitable catheter may be used. For example, the catheters may include one or more lumens and staggered or flush tips. The catheters may include needles or other devices (e.g., imaging devices) located at the distal end, and plungers or any other control located at the proximal end. The catheters and/or other delivery devices may have differently sized lumens to deliver multiple components of the PRP composition in the prescribed ratio. When catheters are used, a physician may navigate to the heart using one of the routes known for accessing the heart through the vasculature, including but not limited to navigation to a heart chamber for epicardial, endocardial, and/or transvascular delivery of the PRP composition.

Endocardial delivery of the PRP composition may comprise accessing a treatment site, for example, in the left ventricle of a heart, using a delivery device advanced percutaneously in an anterograde approach through the superior vena cava or inferior vena cava into the right ventricle. The delivery device may be passed through the interatrial septum into the left atrium and then into the left ventricle to reach treatment site. Alternatively, the device may be advanced using a transseptal procedure, e.g., through the intraventricular septum into the left ventricle. In another embodiment, the PRP composition may be injected directly into the intraventricular septum from the right ventricle. An alternative endocardial delivery method may comprise accessing the treatment site using a delivery device advanced percutaneously in a retrograde approach through the aorta into the left atrium and then into the left ventricle.

Transvascular delivery of compositions may comprise passing the delivery device through the coronary sinus into the cardiac venous system via the cardiac veins and, if needed, leaving the veins by tracking through myocardial tissue. An alternative transvascular delivery method comprises accessing a treatment site through the aorta into a coronary artery to reach treatment site.

A practitioner may make multiple deliveries into various locations using a single device, make multiple deliveries into various locations using multiple devices, make a single delivery to a single location using a single device, or make a single delivery to a single location using multiple devices. The delivery devices may include at least one reusable needle or catheter. Some embodiments may include delivery devices having an automated dosing system (e.g., a syringe advancing system). The automated dosing system may allow each dose to be pre-determined and dialed in (may be variable or fixed). In some embodiments, an iontophoresis device may be used to deliver the PRP composition into the ischemic tissue.

It may be desirable to deliver the PRP composition to the ischemic tissues while avoiding coincidental delivery to other cardiac tissues or other locations adjacent to the heart. For example, the PRP composition may gel or harden upon delivery to prevent migration. In other embodiments, the PRP compositions may be delivered without a gelling agent/activator such as thrombin. In some variations, a balloon catheter may be placed in the coronary sinus and inflated during delivery until the PRP composition has solidified or at least partially immobilized. Other variations may include a pressure control system on the delivery device to prevent pressure-driven migration of the PRP composition. Backbleed may also be prevented by keeping the needle in place for several seconds (e.g., about 5 to about 30 seconds, or about 5 to about 120 seconds) following an injection.

Sensors may be used to direct the delivery device to a desired location and/or to deliver the PRP composition. For example, real-time recording of electrical activity (e.g., an ECG), pH, oxygenation, metabolites such as lactic acid, $CO_2$, or the like may be used. The sensors may be one or more electrical sensors, fiber optic sensors, chemical sensors, imaging sensors, structural sensors, and/or proximity sensors that measure conductance. The sensors may be incorporated into the delivery device or be separate from the delivery device. In some embodiments, the sensors may sense and/or monitor such things as needle insertion depth, blood gas, blood pressure or flow, hemocrit, light, temperature, vibration, voltage, electric current, power, and/or impedance. The sensors may include one or more imaging systems and may be coupled to any appropriate output device, for example, a LCD or CRT monitor which receives and displays information.

The total volume of the PRP composition delivered to the patient may be based on the size of the heart, the amount of the affected ischemic tissue, and/or the desired outcome of the procedure. For example, the total volume of composition injected may be less than 15000 µL.

The number of delivery sites in the heart may be based on the type and location of the infarct(s), the desired location of the PRP composition, and the distance separating the desired locations. The number of delivery sites may range from about 1 to about 25 sites. The distance separating delivery sites may vary based on the desired volume of PRP to be delivered per delivery site, the desired total volume to be delivered, and/or the condition of the ischemic tissue. At the delivery site, the PRP composition may be injected, infused, or otherwise disposed at or adjacent to the ischemic tissue. The PRP composition may also be infused into the vasculature (i.e., vessels) upstream of the target site, so that it will flow towards the affected ischemic tissue.

The location of the delivery sites may vary based on the size and shape of the ischemic tissue, and the desired extent of the treatment of the tissue. For example, the PRP composition may be delivered into the ischemic tissue, and/or into the tissue that bordering the ischemic tissue. Similarly, the composition may be delivered to any combination of the regions of ischemic tissue and other cardiac tissue.

The timing of PRP delivery relative to an acute MI may be based on the severity of the infarction, the extent of the ischemic tissue, the condition of the patient, and the progression of any concurrent MI or arrhythmia treatments. The PRP composition may be delivered at any suitable time. For example, it may be delivered immediately after the onset of an MI, within one hour of an MI, one to eight hours following an MI, or three to four days after an MI after clinical stabilization of the patient when it is safer for the patient to undergo a separate procedure. Treatment may also be done later. The timing may be based upon the level of caspase-3 in the blood. In some variations, the composition is delivered about one week, about 1 to about 3 weeks, about 1 to about 6 months, or even up to or more than about 1 year after the MI. Treatment may be done for patients with congestive heart failure, cardiomyopathy or other heart disorders. Other times for injecting compositions into the ischemic tissue are also contemplated, including prior to any potential MI, and immediately upon finding an area of ischemic tissue. Of course, compositions may be injected into the ischemic tissue years after an MI.

As mentioned previously, a PRP composition may additionally or alternatively be used in other cardiac procedures. These cardiac procedures may include anti-arrhythmia procedures, procedures to correct congenital heart defects, or other pathologies. Examples of other cardiac procedures include, but are not limited to, angioplasty, coronary artery bypass, Minimally Invasive Direct Coronary Artery Bypass (MIDCAB), off-pump coronary artery bypass, Totally Endoscopic Coronary Artery Bypass (TECAB), aortic valve repair, aortic valve replacement, mitral valve repair, mitral valve replacement, Ross procedure, Bentall procedure, pulmonary thromboendarterectomy, transmyocardial revascularization (TMR), valve-sparing aortic root replacement, cardiomyoplasty, Dor procedure, heart transplantation, septal myectomy, ventricular reduction, pericardiocentesis, pericardiectomy, atrial septostomy, Blalock-Taussig shunt procedure, Fontan procedure, Norwood procedure, Rastelli procedure, Maze procedure (Cox maze and minimaze), and/or pacemaker insertion. The PRP composition may be used to prevent an arrhythmia associated with reperfusion of the cardiac tissue during any of the above procedures. As is known, reperfusion may cause a spontaneous arrhythmia to occur after cardiac surgery.

In some embodiments, PRP may be used to treat any lung disease. Examples of lung disease include, but are not limited to: Acute Respiratory Distress Syndrome (ARDS), Alpha-1-Antitrypsin Deficiency, Asbestos-Related Lung Diseases, Asbestosis, Asthma, Bronchiectasis, Bronchitis, Bronchopulmonary Dysplasia (BPD), Chronic Bronchitis (see COPD), Chronic Obstructive Pulmonary Disease (COPD), Collapsed Lung (see Atelectasis), Cough, Cystic Fibrosis, Emphysema (see COPD), Hemothorax, Idiopathic Pulmonary Fibrosis, Infant Respiratory Distress Syndrome (Respiratory Distress Syndrome in Infants), LAM (Lymphangioleiomyomatosis), Lung Transplant, Pleural Effusion, Pleurisy and Other Pleural Disorders, Pneumonia, Pneumoconiosis, Pneumothorax (see Pleurisy and Other Disorders of the Pleura), Pulmonary Embolism, Pulmonary Arterial Hypertension, Pulmonary Fibrosis (see Idiopathic Pulmonary Fibrosis), Respiratory Distress Syndrome in Infants, Respiratory Failure, Sarcoidosis, Tracheostomy, and Ventilator/Ventilator Support. In some embodiments, PRP compositions are delivered directly to the lung via bronchoscopy or delivering indirectly to the lung via the heart or blood vessel. Measurements of tissue perfusion or function may be done to evaluate the efficacy of the treatment.

In some embodiments PRP is useful in treatment of disease and conditions in a variety of tissues including but not limited to heart, lung, liver, kidney, brain, spinal cord, muscle, tendon, bone, skin, ligaments and any other body cell or tissue. Rotator Cuff Tendinitis or Tear, Rotator Cuff Impingement Syndrome or Bursitis, Bicipital Tendinitis, labrum tears, arthritis, instability DeQuervaine's Tenosynovitis, arthritis, other wrist or finger tendinitis, ligament tears or dysfunction of the fingers Illiotibial Band Tendinitis (ITB Syndrome), Psoas Tendinitis and bursitis, Greater Trochanteric Bursitis, Hip labrum tears, Piriformis Syndrome, Sacroiliac Joint Dysfunction, arthritis Patellar Tendinitis, Patellar Femoral Syndrome, chondromalacia patella, partially torn or strained major ligaments of knee (ACL/LCL/MCL), meniscus tears, arthritis, patellar instability Achilles Tendinitis, Peroneal Tendinitis, arthritis, recurrent ankle sprains, other foot or ankle tendinitis Whiplash injuries, headaches related to the neck, arthritis Facet joint arthritis, rib problems, and pain associated with scoliosis. In some embodiments, PRP compositions may be used to treat disogenic spine pain or disorders alone or in combination with other treatments.

As used herein the term "an effective amount" of an agent is the amount sufficient to treat, inhibit, or prevent ischemia and/or reperfusion injury associated with indications and conditions including, but not limited to, myocardial infarction, arteriosclerosis. stroke, septic shock, traumatic shock, and associated with surgical procedures such as vascular interventional procedures including angioplasty, surgery that involves restriction of blood supply to an organ or tissue, abdominal surgery, abdominoplasty, adenoidectomy, amputation, angioplasty, appendectomy, arthrodesis, arthroplasty, brain surgery, cesarean section, cholecystectomy, colon resection, colostomy, corneal transplantation, discectomy, endarterectomy, gastrectomy, grafting of skin or other tissues, heart transplantation, liver transplantation, heart surgery hemicorporectomy, hemorrhoidectomy, hepatectomy, hernia repair, hysterectomy, kidney transplantation, laminectomy, laryngectomy, lumpectomy, lung transplantation, mammoplasty, mastectomy, mastoidectomy, myotomy, nephrectomy, nissen fundoplication, oophorectomy, orchidectomy, orthopedic surgery, parathyroidectomy, penectomy, phalloplasty, pneumonectomy, prostatectomy, radiosurgery, rotationplasty, splenectomy, stapedectomy, thoracotomy, thrombectomy, thymectomy, thyroidectomy, tonsillectomy, ulnar collateral ligament reconstruction, vaginectomy, vasectomy and any surgery involving cardiac bypass, cardiac artery bypass graft surgery and organ transplantation.

In addition to the foregoing uses for the compositions, methods and systems described herein, it will be apparent to those skilled in the art that other injured tissues, in addition to injured cardiac tissue and connective tissue, would benefit from the delivery of structural support materials to treat the injuries. Non-limiting examples of such tissues include the stomach, to reduce food intake and increase satiety; the abdominal wall, to prevent and treat hernias; and the bladder to prevent or treat incontinence. Such tissues may additionally include vascular tissues.

In some embodiments, a specific cytokine, growth factor or drug is administered to the patient to mobilize cells, PRP is prepared from the patient's blood and is used to treat cartilage injuries or disorders such as knee osteoarthritis or spinal disc degeneration.

In some embodiments, a mobilization agent is provided subcutaneously, intravenously or intramuscularly for 1-5 days to the patient, PRP is prepared from the patient and injected intramuscularly to treat the heart or into the muscle of the leg to treat peripheral vascular disease.

In some embodiments, a mobilization agent is administered to the patient and the PRP is prepared. This PRP is then used in an activated or unactivated manner to treat the wound.

It is noted that the PRP may be obtained from the person to be treated (autologous) or the PRP may be obtained from one individual but administered to a different individual.

PRP prepared as described by any of the above methods may be used to provide the platelet concentrations in the following platelet formulations. Further, in some embodiments, the compositions and components for created and utilizing the compositions as disclosed herein can be assembled into kits to be used by laboratory technician, doctor, medical professional, or others assembling such compositions for use.

Platelet Formulations

Example One

Platelets Concentration: 151,000/microliter to 7,000,000/microliter or higher.

CD34+ Cell Concentration: $1$-$3 \times 10^9$ per liter to $100 \times 10^9$ per liter or higher.

Platelet and CD34+ cell concentrations may be at any level in between the above values. The PRP could be unactivated or activated.

Example Two

Platelets Concentration: 151,000/microliter to 7,000,000/microliter or higher.

CD34+ Cell Concentration: $1$-$3 \times 10^9$ per liter to $100 \times 10^9$ per liter or higher.

Platelet and CD34+ cell concentrations may be at any level in between the above values. The PRP could be unactivated or activated.

The composition of example one that includes:

Neutrophils, Lymphocytes, Monocytes, Eosinophils or Basophils in any concentration.

Example Three

Platelet Concentration: 151,000/microliter to 7,000,000 or higher.

Stem cells of any type in any concentration including embryonic stem cells, induced pluripotent stem cells, adult stem cells, and progenitor cell lines of any type.

Example Four

Platelet Concentration: 151,000/microliter to 7,000,000 or higher.

CD34+ Cell Concentration: $1$-$3 \times 10^9$ per liter to $100 \times 10^9$ per liter or higher.

Lymphocytes, Monocytes Eosinophils or Basophils in any concentration without any neutrophils.

Example Five

The composition of example three or four where the neutrophil concentration is less than 100/microliter or less than 500/microliter, or less than 1000/microliter, or less than 5000/microliter or less than 10,000/microliter, or less than 20,000, or less than 50,000/microliter or less than 100,000/microliter.

Example Six

Platelet-rich plasma derived from induced pluripotent stem cells.
Platelet concentration: 151,000/microliter to 7,000,000 or higher.
Pluripotent stem cells in any concentration.

Example Seven

The composition of example six within of any of the compositions of examples 1-6.

Example Eight

The compositions of any of examples above where the hemaglobin concentration is less than 10 g per deciliter; preferably less than 5 g per deciliter, more preferably less than 1 g per deciliter, and most preferably where the hemoglobin concentration is zero.

Example Nine

The composition of any of above examples that include or do not include other stem cells that can be derived from whole blood, bone marrow, adipose tissue or other sources.

Example Ten

The composition of any of the above examples with various concentrations of other white blood cells including monocytes in a concentration of 0, 100-500, 500-1000, 1000-5000, 5000-10,000, 10,0000-50,000 per microliter or higher.

Example Eleven

The composition of any of the above examples with various concentrations of other white blood cells including lymphocytes in a concentration of 0 100-500, 500-1000, 1000-5000, 5000-10,000, 10,0000-50,000 per microliter or higher.

Example Twelve

The composition of any of the above examples with various concentrations of other white blood cells including neutrophils in a concentration of 0 100-500, 500-1000, 1000-5000, 5000-10,000, 10,0000-50,000 per microliter or higher.

Example Thirteen

The composition of any of the above examples with various concentrations of other white blood cells including eosinophils in a concentration of 0 100-500, 500-1000, 1000-5000, 5000-10,000, 10,0000-50,000 per microliter or higher.

Example Fourteen

The composition of any of the above examples with various concentrations of other white blood cells including basophils in a concentration of 0 100-500, 500-1000, 1000-5000, 5000-10,000, 10,0000-50,000 per microliter or higher.

Example Fifteen

A composition that contains platelets in a concentration of 151,000/microliter to 7,000,000/microliter or higher that is also shown to contain stromal-derived factor-1 (SDF-1) in a concentration of 500 pg/ml to 5000 pg/ml, or 100-500 pg/ml or greater than 5000 pg/ml.

Methods of Using Platelet Formulations

The platelet formulations disclosed herein may be useful in treating damaged connective tissue, cardiac tissue, and/or lung tissue in the same manner as described above for PRP. Platelet formulations may also be useful in treating tissues with compromised blood flow, such as ischemic tissue in the legs, arms, brain or other organs. Specifically, acute or chronic limb ischemia may be treated with platelet formulations. In some embodiments, the platelet formulations described herein may repair tissue damage by slowing or halting apoptosis, and that the anti-apoptotic effects of the platelet formulations may be measured based on a decrease in caspases in the blood, such as caspase-3. In some embodiments, the platelet formulations may be applied in conjunction with reperfusion therapy.

In some embodiments, the platelet formulations disclosed herein may be useful in treating ischemia, cancer, a disease of the immune system, a connective tissue injury, a skin disease, or a disease of the nervous system. The platelet formulations may be useful for the treatment of acute or chronic skin conditions such as burns or wrinkles. The ischemia may be a brain ischemia or cardiac ischemia. The cancer may be brain cancer, thyroid cancer, pancreatic cancer, liver cancer, breast cancer, or prostate cancer. Other types of cancer or neoplasia may also be treated with the described platelet formulations. The connective tissue injury may be a tendinosis, such as tennis elbow, rotator cuff injury, a knee injury, a spinal injury or plantar fasciitis. The nervous system disease may be Parkinsons' disease or other neurodegenerative disorders such as Alzheimers or Multiple Sclerosis.

Method Example 1: Use of PRP to Obtain and/or Differentiate Pluripotent Cell Lines A skin biopsy (or any other appropriate tissue) is taken from an individual and then his or her fibroblasts (or other cells) are cultured. PRP is then prepared from the whole blood of that individual or another individual and specific bioactive molecules such as vascular endothelial growth factor or a bone morphogenetic protein (or other appropriate cytokines, chemokines or growth factors are isolated). These molecules are then administered via a variety of methods to the fibroblasts and nuclear reprogramming to a pluripotent cell line is achieved.

Alternatively, an established pluripotent or multipotent cell line is treated with PRP with or without specific fractionation to induce differentiation of that cell line. Additional exogenous factors or methods may be added as needed to accelerate or complete the differentiation of that cell line. Different preparations or compositions of PRP may also be used to accomplish the task. In some embodiments, the preparations and compositions of PRP can be similar to but not limited to those as described herein. PRP may further be used alone or in combination with bone marrow concentrate, or fractions of adipose tissue. In some embodiments, some fractions of adipose tissue can include adipose tissue that is a source of mesenchymal stem cells and endothelial progenitor cell or other adipose derived stem cells as well as other cell components including preadipocytes, T cells, B cells, mast cells, adipose tissue macrophages, and other cells known in the art to be in fractions of adipose tissue. In some embodiments, the cell line or stem cell line can be treated with a composition containing platelets at a concentration of 151,000/microliter to 7,000,000/microliter or higher in combination with bone marrow concentrate and/or any fraction of adipose tissue.

In some embodiments, the composition can include progenitor or precursor cells combined with the PRP composition to aid in acceleration or completion of the differentiation of a cell line. Progenitor or precursor cells in tissue are partially differentiated, usually unipotent cells, which give rise to the differentiated cells. The progenitor or precursor cells may have lost most or all of the stem cell multipotency. Progenitor or precursor cells can be combined with the PRP composition to accelerate or complete the differentiation of a cell line. Therefore, in some embodiments, the cell line or stem cell line culture can include a composition containing platelets concentration of 151,000/microliter to 7,000,000 or higher in combination progenitor or precursor stem cell lines of any type including mesenchymal stem precursor lines.

In some embodiments, the cell line or stem cell line culture can include a composition containing platelets or PRP in combination with embryonic stem cells, induced pluripotent stem cells, adult stem cells (such as mesenchymal stem cells), and or progenitor cell lines of any type. The composition containing platelets can have a concentration of 151,000/microliter to 7,000,000 or higher.

The cells lines would be carefully monitored for differentiation by surface markers or other measures of cell specificity. PRP could further be used to accelerate proliferation of the cell line. One specific example would be to create functional human platelets from induced pluripotent stem cells alone or then use them to create platelet-rich plasma of any composition. The iPSC would first be differentiated into megakaryocytes via a variety of vectors. Concentrated platelets would then be harvested and suspended in plasma, saline or other biologic media. In some embodiments, the PRP produced with this method can be a composition of platelet rich plasma derived from induced pluripotent stem cells at a platelet concentration of 151,000 to 7,000,000 or higher and pluripotent stem cells in any concentration or form.

Further, in some embodiments, the compositions and components for created and utilizing the compositions as disclosed herein can be assembled into kits to be used by laboratory technician, doctor, medical professional, or others assembling such compositions for use.

Method Example 2: Cell Differentiation Using Platelet-Rich Plasma

Glioblastoma cells (012705), a cell type with severe dedifferentiation and an anaplastic phenotype were cultured with and without 10% PRP for 10 days. At 10 days, dramatic differences were noted in the phenotypic expression of the cell lines.

Without PRP, the cells continued to be of an anaplastic phenotype. With PRP, the cells differentiated into a mature phenotype resembling an astrocyte. See FIGURE.

Further, in some embodiments, the compositions and components for created and utilizing the compositions as disclosed herein can be assembled into kits to be used by laboratory technician, doctor, medical professional, or others assembling such compositions for use.

Drug Discovery

Platelet-rich plasma (PRP) could be used to identify or validate a new drug. Specific targets such as proteins, genes, RNA, microRNA, or epigenetic modifications or markers would be tested using whole or fractionated PRP of any type or formulation. Assays would be developed using PRP to look for disease associations, genetic expression, phenotypic or genotypic alternations in-vitro or in-vivo markers. Specific fractions of PRP could also be developed by blocking specific growth factors to create more bioactive PRP. Importantly, novel factors within PRP could be identified, purified and either used therapeutically or created via genetic engineering techniques to produce a drug. Drugs could further be tested in cell cultures that use PRP as part or all of the growth media. Toxicity or potency of a drug could further be measured its influence on PRP. Specifically, PRP could be used in target identification and validation of drugs.

PRP Potency

PRP potency could be measured visually by observing over time the chemotaxis of stem cells or other bioactive molecules. PRP potency could also be simply measured by visually quantifying platelet interaction with other cellular components or via the activity of platelets to a known agonist such as calcium, collagen or thrombin. This could be done via single observations under a microscope or via time lapse photography to measure cellular movement or chemotaxis. Time or completeness of platelet activation could be another endpoint. For example, in some embodiments, the potency of platelet rich plasma can be visually observed over time by any method known in the art or described herein including but not limited to cellular movement, microfluidics or chemotaxis. In some embodiments, the measurement of PRP potency can be observed via visual means such as a microscope or its activity in relation to other cells.

What is claimed is:

1. A method of preparing a platelet-rich plasma (PRP) composition comprising:
    isolating platelets at a concentration of 151,000/microliter to 7,000,000 per microliter to obtain PRP, and
    adding CD34+ cells at a concentration of $1-3\times10^9$ per liter to $100\times10^9$ per liter to the PRP to obtain the PRP composition.

2. The method of claim 1, further comprising the steps of:
    determining the concentration of stromal-derived factor in the PRP composition, and
    adjusting the concentration of stromal-derived factor-1 (SDF-1) in the PRP composition to a concentration of 100 pg/ml to 5000 pg/ml.

3. The method of claim 2, wherein the concentration of SDF-1 is adjusted to a concentration of 500 pg/ml to 5000 pg/ml.

4. The method of claim 1, wherein the platelets are isolated from whole blood.

5. The method of claim 4, wherein the whole blood is obtained from spleen.

6. The method of claim 1, wherein the neutrophil level of the PRP is less than 5,000 /μL.

7. The method of claim 6, wherein the neutrophil level of the PRP is less than 1,000 /μL.

8. The method of claim 1, wherein the PRP contains a lower concentration of red blood cells or hemoglobin than the concentration in whole blood.

9. The method of claim 1, wherein the PRP contains a higher concentration of white blood cells than the concentration in whole blood.

10. The method of claim 9, wherein the white blood cells comprise higher concentrations of lymphocytes and monocytes compared to whole blood and lower concentrations of neutrophils compared to whole blood.

11. The method of claim 1, wherein the platelets are obtained from spleen or bone marrow.

\* \* \* \* \*